(12) United States Patent
Chen et al.

(10) Patent No.: US 10,994,005 B2
(45) Date of Patent: May 4, 2021

(54) METHOD FOR PREPARING A K SERUM WITH A VIBRIO PARAHAEMOLYTICUS AS AN ANTIGEN

(71) Applicant: Zhejiang University, Hangzhou (CN)

(72) Inventors: Yu Chen, Hangzhou (CN); Xiao Chen, Hangzhou (CN); Qiaoyun Zhu, Hangzhou (CN); Guoliang Xie, Hangzhou (CN); Ruonan Wang, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 16/771,693

(22) PCT Filed: Jul. 30, 2019

(86) PCT No.: PCT/CN2019/098261
§ 371 (c)(1),
(2) Date: Jun. 11, 2020

(87) PCT Pub. No.: WO2020/237817
PCT Pub. Date: Dec. 3, 2020

(65) Prior Publication Data
US 2021/0052716 A1    Feb. 25, 2021

(51) Int. Cl.
*A61K 39/02*    (2006.01)
*A61K 39/00*    (2006.01)

(52) U.S. Cl.
CPC ...... *A61K 39/107* (2013.01); *A61K 2039/521* (2013.01)

(58) Field of Classification Search
None
See application file for complete search history.

(56) References Cited

U.S. PATENT DOCUMENTS

2009/0226895 A1    9/2009    Leung et al.

OTHER PUBLICATIONS

Li et al. 2016 (Vibrio parahaemolyticus strains of pandemic serotypes identified from Clinical and Environmental Samples from Jiangsu, China; Frontiers in Microbiology, vol. 7, article 787, pp. 1-13 (Year: 2016).*
Chen et al. 2018 (A New Serotype of Vibrio Parahaemolyticus Is Becoming the Main Epidemic Strain in China (Nov. 30, 2018) Available at SSRN: https://ssrn.com/abstract=3294765 or http://dx.doi.org/10.2139/ssrn.3294765) (Year: 2018).*
Dongsheng Han et al. Spreading of pandemic vibrio parahaemolyticus O3:K6 and its serovariants: a re-analysis of strains isolated from multiple studies Frontiers in cellular and infection microbiologyMay 18, 2017 vol. VII ISSN:2235-2988, entire disclosure.

* cited by examiner

*Primary Examiner* — Mary Maille Lyons

(57) ABSTRACT

A novel K (capsular antigen) serotype of *Vibrio parahaemolyticus* and an application thereof are provided. A novel K (capsular antigen) serotype of *Vibrio parahaemolyticus*, which was deposited at the China General Microbiological Culture Collection Center (Institute of Microbiology, Chinese Academy of Sciences, No. 3, Yard 1, Beichen West Road, Chaoyang District, Beijing) on Feb. 20, 2019, with a deposit number of CGMCC No. 17249, wherein the K epitope of the *Vibrio parahaemolyticus* has a sequence set forth in Sequence No. 1. The novel K serum is highly specific, and can be used to conveniently and quickly detect a novel K serotype of *Vibrio parahaemolyticus* (O4:KUT-recAin) which has a rising infection rate in recent years. It provides important detection techniques for the pathogen diagnosis, monitoring and prevention of infectious diarrhea.

2 Claims, 8 Drawing Sheets
Specification includes a Sequence Listing.

SEQUENCE LISTING

<160> NUMBER OF SEQ ID NOS: 1

<210> SEQ ID NO 1
<211> LENGTH: 35462
<212> TYPE: DNA
<213> ORGANISM: Vibrio parahaemolyticus

<400> SEQUENCE: 1

```
ttaactgttt tggatagtta agtattcggc aacgccttct gcaaccgtct            50
tgaactcaac atcgcaaccg gcagcgcgta gcttggtaag gtctgcttgc           100
gtgaactctt gataggcacc ttttagatgt tctgggaaag gaatagtttc           150
aatctcgcct tttccatgat gggtaatgac cgcttttgct acttcttcaa           200
aagattctgc acgaccagta ccacagttga agatgccaga aacaccattt           250
tcaaggaacc acaggtttac tttacataca tcaccaacgt aaacgaaatc           300
acgcttaaaa gactcgctac ctgcaaacag ttttggattt tcacctgcgt           350
ttagttggtt gttcagatgg aacgcaacag atgccatgct gcctttgtga           400
tcttcacgtg ggccatatac gttgaagtaa cggaagccgg tgatttgaga           450
aagggtctca ccatgttctt cagcgtcttg ccatagacga cgaacgtagt           500
tatcaaactg ctgtttcgag taaccgtata catttagtgc gccttcgtat           550
tcgcgttctt caacgaaagt atctgtatcg ccgtaagtgg ctgcggaaga           600
ggcgtatagg aatggaattt cacgatctaa acagtaatga agcagctctt           650
tagagtactc gtaattgttt agcatcatgt atttaccatc ccactctgtc           700
gttgcagagc aagcgccttc gtggaaaatt gcctcaatcg gaccaaaatc           750
atcgcccgcc ataatttggg tcagaaagtc gtcacgatcc atgtaatctg           800
tgatgtccag atcaactaag ttcttaaact ttttgccatt ttttaggttg           850
tcgacaacca agatatcgtt aataccagct tcgtttagtg ctttaacaat           900
gttgctgccg atcatgccag cgccaccagt tacgatgatc atagaacttc           950
caccatagat taaatttttc tcaggaattc tagcaagaaa cagaaattag          1000
cgctattgga aggaaaagaa aggtatagag tgcagggagg taagaacaaa          1050 caaagggag ccgaagctcc ctttaatagt gttgttattc agcgtttgac           1100
gcgtttggtc tttggtacca agggttacgt tcatcagtaa gttcaatcaa          1150
gctgtacttg cgacctagct tctgaccgcc atcacgagtc agtggctgcc          1200
agctaaagaa cgcgcggttg ttgcttggtt tcaccgtcat aatgtcgaat          1250
ggaatcgaaa tgtagaagcc tttagtaaag ctaccttcac caaattcgtc          1300
agcagacaag tcactgattg atgcgaatgc accagcaatg acaccactct          1350
tgaactgttt agatacattc acttgtgtac cgatatcacc cgctaggaac          1400
tgaccaatat caacttgaat catcaaatct tgtaggaagt cccattgagg          1450
gtagtaataa cccgacacaa aaccagtaaa gcctttgtct acaacttgga          1500
acggacgccc atattctgga acgtattgcc atttctcatc gtatacaccg          1550
aagtagcttt gcgggtcacg ttgagagatc aagtttacat ctgcaccgat          1600
cgcccagttt gcgcctttcg gtcggtacaa gaattcggta cccacacccg          1650
```

```
cgaacatact ttctagataa ccagcgtaga actgttggtc catggtgtct        1700
gagtactctt ggaaccaagt taactgcagg ttggacatgg ttaccgcgtg        1750
ttcattttga taagcacgga acatggtacg tacacgagga atcgaagtgc        1800
catccggtgg ggttacgtag ttaaacttgt cgtagttgtt gtaccaatcc        1850
cagtatagcg agccaccaat ttctaggtta tctgtcagcc agtaagaggc        1900
gctgccactt agaccaacac tgaacaagta gaactcttct gggttgccca        1950
aggtctgagc cagttttggt gagaagcccc aatcaaagcg ctcaaaacca        2000
tcgaaagcag gtttgccttg cggtttatca cttgaggttg atgttgcatc        2050
ttcgatattt ggattgatgt agttaacttc tgcaaagtca cggtatttct        2100
ctttggagat aaccgtttga tcgccgatca gaccgcgact gcgttcattg        2150
atcgtaaagg tatcaatgtt gtctggcatt tcgttgtaaa ggactgccgc        2200
tgcttttca tgagcctcgt tgcgatcacg atacttttc tgctcgccga          2250
caaccgaaac ggtattgtct tcaacataga gttgggtatt ttggtagcca        2300
gcaatcttat ctagctcctc ggtaacacgt tcccaatcta catcagacag        2350
ttgctctggt tgcttgtctt caacttctgg tgttggtgta tcacgccaga        2400
aagacggcat atcattgaag tttgtgtaaa ggcttacgcc tgccactaac        2450
atatcgccgc gctcgtagct caagcgcaca tctgccatat gtcctaagcg        2500
atacaaaaca ccaaagttcc aaggcgtatg aggtgtcatg tctacaccac        2550
cgcgtaccac agggaaatct tcgctgtaat cgttgctgtc gtattcaaac        2600
ttaaatcgca gtggtgcgtg caaagtttga tactcgacac cgccaaagag        2650
tgctgcagga cctttgaacc agcgttcaaa atccacacta ccgccattac        2700
ctttaaagtc tgaagggcgt tcacagaaac tatcggacag cttacaagct        2750
gggttgctga tgttgtcgcg cgtacctaag tagccccagc ccatacctaa        2800
agtgaaatca aaggtaccaa ggtttgggtt agagtaacgc tttgtcgcag        2850
caacaaactc accatcaaaa agaccggtgc ctgcaaagtc acgcacaccc        2900
acagaaagct ctggcaagta ctctgactct tgcaaaagtc gaactttaaa        2950
atcgatacct ttgtcggtgt atttggtatc accggagaag cttgggtcat        3000
cactataaaa aagatcattc accatggtgt agcggatggt cgtttctaac        3050
cagggcatga cttgcagtgt gacattgtaa aaaaggtact catcgctgac        3100
ggtaacagca aaattaaact cgccttcagg tgccatacga cctgtgggca        3150
tctgcattaa gccgacacca ccaaagtcca tttgtgacgg ttgtaatggt        3200
ggtgcttcga aaggcacgtc ttgagcccat accaacgctg acccattaa         3250
agaaagggat agactggttc tgatcaggtt catgtttagt tcttcgatga        3300
ggttggttta cgttgtgcaa gcagagcgac aatgtcttta tccatttgtg        3350
atgtttcgaa ctcatcaaaa gggatgtaca ccatggtaag tggtggcaag        3400
taatattgag tggttaccca actgccatgg tgaggatgaa cgaccttgcc        3450
atctgggtaa atcaggactg gtggataagc aagtttacca atatcgcttg        3500
aacctagata atcgacctgt tcatgcagag cgatacccgc ttggttttct        3550
accgcgtaga cttttctaa gttccccaca tacagcactt tctctttgcg         3600
ttttggtgca cttaacgcaa gttgaccttg taaaagaggg ttctcaaatt        3650
```

-continued

| | |
|---|---|
| tatccagacg gatgcgatca acatcaatgg ccgacagcac gcgaggtgca | 3700 |
| aactggcttt gttggataaa cttgtaaaat gggtgtgcaa ctaaattatg | 3750 |
| ttgaatcatt tggttcaaca ccgaattctt taaggcagta ctttcttgca | 3800 |
| ctgctgtttc ggaattatca aatagagtca cagctaaagg gtattgcagg | 3850 |
| gtgacttgtt gttcttgtgc atgcttaagt acgctctcta attgtgccgc | 3900 |
| ttgttggaac tgcaatgctt tgcctgttcc gacaagttct atattgagcg | 3950 |
| gtggtgtggt gtgattttga gcttgaacga tagtaggtgt cgccagaatc | 4000 |
| gttgccgtta aacttaggct taataaagat agcagtcgct tattcatgat | 4050 |
| ttgctgtacc ctttcagaat cgtcaattca acgggcacca tgtttggacc | 4100 |
| taagtgttga cgtgttttca ctacttctcc tttaccgttt acccagtatt | 4150 |
| ggttctctac actttttttct aagctggtaa acgttacaac ctcggtataa | 4200 |
| acatcagtag aggtagatga aatagggtg atgacggttc ctttaccttg | 4250 |
| atgagaacgc tggactttag ccgggaatcc ataacggtat tgtcagacc | 4300 |
| aatcgtaaga aagagaatat tgtgcagagg gcgctgagta ggcaggaacg | 4350 |
| ttgccataaa tgcctgctag attggtggtt tgcaagccaa tagttttaac | 4400 |
| gatatgaccg ttttctgtta ccaccatcgc cttgtctgca cttacccact | 4450 |
| ttaactgggt attgccagtt agtgggtttt gctcagcaaa ggccaacact | 4500 |
| acgaagacct gttttggtc accaattttt aagtatgcac tggcataagg | 4550 |
| aaccgcttca atttcttctg gcgttagttc gacatcgatg tagttgccat | 4600 |
| aagcttcttg gactgttgcg gatacgtcat taaattttg tgtacagcca | 4650 |
| aagattgagc tcagtaaagg tagggcaata agtaagcgca tccattttag | 4700 |
| cgatagaaag gtgttcatca ttccctcatt acaaataaaa tcgccctgaa | 4750 |
| tagatcaggg cgattgtttc catatctaca aactaaaaat tatttagtta | 4800 |
| ctggagcaga agtagacgta gaagtagacg ttgaatcgct gtctgacgcc | 4850 |
| gcaactgcta ctacagttac tgctgctgct gcacctactg ctactgcagt | 4900 |
| tgtaccagtt gcagatgctg ccgctgtgcc tgctgtacca gcttcagtcg | 4950 |
| ctgcaaatgc tgttgatgcg cttagagcca taagaatagc tagagctgta | 5000 |
| ttcttcatta ttaatccttg tatttcagat tttaaaacat cgatgtttgg | 5050 |
| tctgtttata acataccacc tctcatttta gttaaaaaac aatcagcatg | 5100 |
| taaatagttt cctatgcgaa tttacctaat gctaaagaaa gaccgtggaa | 5150 |
| gaactgagaa ttcgctacgt gggattcttg tattttataa agatgcacat | 5200 |
| cctattgctt aagcttaagt caactctgag ttcgcgcaaa cgttcacggt | 5250 |
| ttttattcca gcaatccctt gttgtatctg cttttgagtc gctgatagtc | 5300 |
| aatgctttc ttatttgtga gaatttactt accataaaca gaactttgag | 5350 |
| aaggtctcac cctattgccg ttttgcgcta atccatgcat aatttgccag | 5400 |
| cttttgtgtg gcgtttatca agactatttt tttgaacgac tagtcgcaaa | 5450 |
| agtgaggctt gaaaagaata tttatatcaa taaaccgaat gagatcggga | 5500 |
| atcagcgaac agtggctaac gcgtaatgcc gccgggcggt agcgtgaaaa | 5550 |
| cgcacaagcg aaattgacaa aagttaacag acattcactg cgcgcgtcat | 5600 |

-continued

| | |
|---|---|
| tcataatgtg ctgcggtcag tcgacaccca aggaacactt acgtgattaa | 5650 |
| taaacgacca tggctagggg cgttgagtgc aatcagctta ggcttgtgct | 5700 |
| cattttcggc ctcagcagat ttttatgctg gtgcgttagt cagttactct | 5750 |
| aacgccgaat tcttcattc ctcttcttca gtaaccgagg gaaacccttt | 5800 |
| ccttctacaa gcgcaagctg gttacttctt caatgactac ctcgcttttg | 5850 |
| aagcgcgtta cggaacttct gtacaacgag acaatggact tgcagtagac | 5900 |
| agcctagcga gtggctttct taagctgaac atgcccgtct ccgaacgtat | 5950 |
| cgcactgtac ggacttgctg gttattcgag cgttcagatc gaccaacaaa | 6000 |
| atgtaggctc aaataaagct caaggtttta gctttggttt aggtatgcat | 6050 |
| tacgccttag acaagcagaa tgcgattgtc tttgagtttg ttgattgtac | 6100 |
| atctgaagat caggttcgct tgaacgcact tacttttggc tttcaacacc | 6150 |
| gattttaatt aaagacctag tgcctagttt tgtggctagg attttaact | 6200 |
| cctgacttta aatagcgaat tatcatgctc aaaggatatt tctcgatagg | 6250 |
| tgcttgcatt ctggcaagcc tatttgcgcc gtttactaat gcgcagactc | 6300 |
| caacccccaga acaaattcag atgtttcaga acttacctgc tgaccagcaa | 6350 |
| caagcgttgg cgagtaagta tggtatctct attccatccg gagcttcttc | 6400 |
| tctgccaagc agttaccaaa atcctcaagt ggttgagccg cgtccaattg | 6450 |
| ctagcagtgc gactgaagta aaagtaaccg actcagaaaa agaggagcaa | 6500 |
| ggtctaaagc gttttggttt agatctattt gctggttcac ctacgacgtt | 6550 |
| tgcaccaatt agtgatgtgc ctgttccggc tgactacacg gtaggagctg | 6600 |
| gtgatgaaat cgttatccaa cttttttggta aagagaacac gacgcatcgc | 6650 |
| cttcgtgtta atcgcgctgg tatcattaat ttcccttctc tggggcctgt | 6700 |
| tcaagtggct ggtatgacat tctctgacgt gcgcgattct ttaaatcagc | 6750 |
| gtgtaaaaga gcaaatgatc ggggttcgca gtgatatttc gttaggtgaa | 6800 |
| atgcgtacca tgcaagtttt tgttatgggt gatgcctaca agccaggtgc | 6850 |
| ttacacggta agtgccctaa ccacgatctc tcaagcgatt tactatagtg | 6900 |
| gtggctttag tgaaagtggc gcccttcgta acgtgcaact taagcgcaat | 6950 |
| ggtcaggtaa ttcgtaaact tgatatgtac gacctgttac ttaaaggtga | 7000 |
| tgcgcgtaac gacatccgct tattaccagg agacgtggtc ttcatcggtg | 7050 |
| cattgggtaa cactatttcg attgatggtg aagtaaaccg cccggcaatc | 7100 |
| tatgaaatca aaccaggtga aacttataag caagcgattc aaatggcggg | 7150 |
| tggttttacg gctaacgctt atagcgatca aatcgaagtg aagcgttacg | 7200 |
| ccgaaaaagg tgctcgcgat gcattaacac tgaactttag ccagtcacat | 7250 |
| gaccaacaaa ctaaagtcaa agatggtgat gcggttaatg tgcttaagaa | 7300 |
| aaatgaagaa ctgacccgtt acgtacaaat agaaggtgat gttcgtcatc | 7350 |
| cgggctttat tgagtggaag agcggtctgc gtattgcaga tttattccaa | 7400 |
| tccgttgata cctcatttaa ttctactgca gatgtaagct atgccgttgt | 7450 |
| tgtgcgtgag attaatcctc aacgcgatat tgaggtttac caagttaacc | 7500 |
| ttgctaatgc gattctttct ccaacaagta aagataactt gaagctgaat | 7550 |
| tctcgcgatc gagtcttggt gtttaaccgc ttcaataatg aagatttaga | 7600 |

```
tacattagcg gaccaacaga cagttaccaa agcgaaaacc ttagagcagg         7650
ctcaacttca agcacaacaa gaacagttga aagagcaaga agtcatgagc         7700
tcatcagtgg cggtgtcttc tgcgacgcca ctagaaaaag attcaaagca         7750
accaaagatc gtgctccgtg gtaaagaaat cactaaagat gactttgaag         7800
cattaaaaca aaatacgcgc cgtacgttgc ttgctcctgt gctgctgcaa         7850
cttcaacagc aatctcgttt aggtttggct ccgcaaattg cagaagtctt         7900
cggtgaggta aaacaccctg ggcgttaccc aattacccca cgtatgacga         7950
tttcgacctt aattgaagct gcgggtggtt taacttataa cgcatttacc         8000
atcaacgccg agttagctcg tacggtaatt aacagtaaag atgagcgcgc         8050
ttctattgat gttgagcgta ttgatttgcg ccaagctatt caaggaagta         8100
ctgttgccga tgccattatt gttggcagag accgcttaaa catccttgag         8150
aagccaaacg tcaaactgca agcacggta acattgcaag gtgaggttcg          8200
cttccctggt acttacactg tccgccaagg tgagacctta ggtgagctgt         8250
tagagcgtgc tggcggctta actgaatttg cacacccaca aggggccatc         8300
tttactcgtg aggctttgcg ccttcaagag caaaagctac taaaccaata         8350
tgctgcagat atgcgagcag aaactgcgaa gaaaaccttc cgcgctgata         8400
gtaatatggg ttcagtaatc tcagacccag ataagacact gaagtttgtt         8450
gaagaagcaa gtcgcagcaa agctcttggt cgtatggtcg tacagcttaa         8500
tcgcattcta aaagacgagc gttctgcaga ctttatgtta aagatggtg          8550 acttcctatt tgtaccgacc ttccgaaata cagtttcgat tatgggtgaa         8600
gttcaagttc caattacata tctgctggat aacaaactag atgtggacga         8650
ttacttgaac aaagccggcg gtgcgaaaaa acaagcagac gaagaccgta         8700
tcttcgttgt gcgtgcagac ggctcggttt acaaccaac atcaggctac          8750 tggttcggta acaatcatga agagctaaaa gctggtgata ctattgttgt         8800
accaatcgat acggactacc gtgatgcatt aagcacttgg actgcagcta         8850
cgcagatcct ttaccaaact ggtgtagcga tcaacgcgtt gaagtaagga         8900
acgacaagat cattccaatc agcttaaaac aagattagaa atgcaataat         8950
agtaagagct tatgtaacga ttgaagttac ataagctcag ttttatgaac         9000
atgattaatc aaaacggcaa atactactct gaacacaata gtggcattat         9050
tcagccgtag cccgtcattc cagcgagccg aagcgagact agaaatcttg         9100
tcacagcgcg gttttttga  aagtcggaga acaatctacc aaatttcacc         9150
aatctctgag tccaatataa cgaacctcag agcttaggat taaatactaa         9200
tggaaacaca aaaagaaccc aatccaaatt atctaccata cccacctcaa         9250
tcccagtcca ctgacgatga aatcgactta cgtgagctct ttaaagtctt         9300
atggaaaggc aagtggggca ttatcgcgac aacatttgtg tttgctatag         9350
gttccgtatt ttatgccttg agtcttccta atatctataa agccgacgct         9400
ttattagccc ctgcagaaag ttcaaatgga ggtggtctat caaaaatggc         9450
cagtcaacta ggcggtcttg cagcattggc tggcgtgaat cttggtggtg         9500
gtgaaacatc acagacagat ttagccgtac aagtgattaa atcgcgtcaa         9550
```

-continued

| | |
|---|---|
| tttataaaag attttgtcaa taaacatgat ttattagttc cacttatggc | 9600 |
| agttaaagac tgggatctat cgaataataa actaatctta aatgaacaaa | 9650 |
| tttacaaccc ggtaactaat gaatggttgc gtgaagcaaa aggtcttcga | 9700 |
| ggttcaaaac ctactacgca agaggcgttt gagatcttta gtaaggatat | 9750 |
| actgagtatt aaccaagata aagaaagtgg cttatattct gtgtccgtta | 9800 |
| aatattattc tccttatatt gcaaagcaat gggttaactg gttaattgaa | 9850 |
| gacatcaata atgttatgcg cgagcgtacg attgctgaaa cgtcacaaaa | 9900 |
| tctagcctat ttaaacactc agctacaaaa aactgctgtt actgatatgc | 9950 |
| agagtacctt ttataagtta atcgaagatc aaactaagag tttaatgtta | 10000 |
| gcagaagttc aggatgagtt tattttcaaa gttatagatc ctgctattac | 10050 |
| cccagaaata aaattcggac cgaatcgagc gttgatttgt ctattgggga | 10100 |
| ctctgttggg aactttattg ggataatttt ccattttttat tttgtatgta | 10150 |
| tttagaaaat aaatatcaat attaatcttt tttctattaa tggttaccta | 10200 |
| aataatcaac aaattatatc ttgagttttt aaatacttga gatgaaatga | 10250 |
| atcacgctta actattagct ttttatatca ataatgcgtg atgtttaagt | 10300 |
| aattgactaa aggcttgaat atgtccgttg aactttatt tttaggagca | 10350 |
| ggtaaacctg taagtggtaa taaacctgca gcgctaaaaa ttattactaa | 10400 |
| caatactaaa gctatggatt ggcagcttca tagtttcgaa gatgttgctg | 10450 |
| aacttagtaa tacatacttt ttaggtggct atcacgtcga agaagttgtt | 10500 |
| aaagaatatc ctagtttaaa ctttagtgtt ataccagatt gggataaatc | 10550 |
| aacagcgcta gatacacttt tgcatgctcc tttttctggg aagccggtca | 10600 |
| ttatatctta tacagatacg ttatttagaa aggaatttat aaacaaacta | 10650 |
| atttctgacg attctgatgt aactgtagtt atcgatagcc aatggcgaaa | 10700 |
| gcgtttcaaa tctcgtagtc atatagatat actaagtgca gaaacaatgt | 10750 |
| atgttgacaa taaagaagtc gaatttactg gtttggtgta tctaagtcca | 10800 |
| ttggccgtgg aaaaaataag acgagtcttg gttaatgaag atgtaaaaaa | 10850 |
| aataggaaaa aacctattag atgcaattag ttttttgaaa gagcaaagct | 10900 |
| taaaattttc ctttaaagat atcgagggag actgggccga gtttaactcg | 10950 |
| acaacagata ttgctaattt tattttagga acaaaagctg acacacttgc | 11000 |
| gagattagaa tcaatagtaa aaaaaagcaa aataggaaag caagaaagtt | 11050 |
| ttacgactaa acaatggatg gatagtaaag aaaaaataat ttcaaatatc | 11100 |
| cagaatcaat ttggagatac aaagttagtt gttcgcagta gttcaaaagc | 11150 |
| agaagataac tggcgatctt ctaacgcagg tggttttgaa agtatcttaa | 11200 |
| acgtgagctg tttggataac acctccctag aaaaagcaat tcaagatgta | 11250 |
| gttgactctt atggctaccc tttacttgat aatgatcaag tactagtgca | 11300 |
| agagtttcta caagatgttt ccatggctgg ggtagttttt acctgtactt | 11350 |
| tagagtctgg agccccttat tatcgcttta acttcgatga ttcaacgcag | 11400 |
| tctacagagt ccgttaccgc cggaacacat atcgacttaa gaactgtgat | 11450 |
| cgtaagtaag ttcaaccgc aagcaattgc gcacattgct cctgaattaa | 11500 |
| ccggtgtact aactgcgata caagaattgg agacattatt aagttttgat | 11550 |

```
aagttagaca ttgaatttgc agttgactcg ttggggcaag tacatatatt    11600
tcaagttcgt ccggtagttg taaatcatga taattatgag atggatataa    11650
agaaaatatc atcatcaatt cagtctgatg taacacgcta tcaaaatctc    11700
caaaattcat tacccttat tagtggcgat agaacaattt ttgcgaatat     11750
gcctgattgg aatcctgcag agatcattag tactaggccg aaacctttag    11800
cattcagcct ttatcaacac ttaattacta atgaagtatg ggcgactcag    11850
cgtgctgaat atggatatcg aaatgttaaa ccttatccat tgattatatc    11900
attttctggt cagccttata ttgatgttcg agctagtttt aattctttca    11950
taccaagttg tgttcctaat aatagtgcaa gtagaattgt taacgcttat    12000
ttagatatat tgtcagataa ccctcagctt cacgacaaaa ttgagttcga    12050
tgttgcattt actatttgga ctcctgagtt cttagattct gcaaaaaatc    12100
gtttaattcc ttatggggtt ttagaaaaag atatctacga gttagaaaaa    12150
ggtctcaaag agataacaaa aaaagcactg acgagattgg atgatgatat    12200
aaactccatt actattctta atgaacgatg cgagcaaatt tgtaaatcta    12250
atctgaatgt tgtcgataag gtatttgctc taattgatga ctgccgacgt    12300
tttggtacgc ttgcgttttc acatgctgca agagcagggt tcgttgcaac    12350
gacgttaata aaaagtttag tgaaccaagg agctctttcg gaagagagac    12400
gtatgaaatt cctaaatagt tttaatactg ttgccggtga gtttgaaata    12450
gataaatcaa attacttaat cggtctagtt actgaaaatg agctaattga    12500
aaaatatggt cacttgagac ctggcacata tgaagttacg actcaagctt    12550
attgggaaga cccgaagcaa tatctacttc caaatggaag caaaaaaaac    12600
agtgagcact gtatagagtt tgcatttagt aacgttgaaa aatcagagat    12650
gtacaaattg atatccgaac ttggttctga gatttcggta gatgaattta    12700
ttaaatatct ggttaaagct actcaagaac gtgaaagagt taagtttgaa    12750
tttacacgta accttagtcg tgcgttagac ttgtgtgtgg agtttggtaa    12800
agaagttggt attagtcgtg aagatatatc tttcttaacg tatggagatt    12850
tagaatgctt aaaactaaac actaaatcat ttgagcagtt gaaaagcata    12900
gttcaagaaa ggaaagagaa atatcaaatt acaaaagcga ttgaactacc    12950
atctgttatc gactctcctt caaagttttt ttgcttcgag agagaatcat    13000
cccaaccaaa ctttgttgga gttaataaag ttgttgctga agttagacga    13050
attgaaggcg ctgaaaagaa agatctttct gggaaaataa tcataattcc    13100
acaagcagat cctggttatg attggctttt tagccataat attaaaggac    13150
taattacttt atatggaggt gcaaattcgc acatggctat ccgttcagca    13200
gaaattggat tgccggcggc gattggggtt ggtgaaaagt tatatgattc    13250
attattaaat gttgagcgaa tagaattaga ttgtttaggc aagacgctaa    13300
gagttataga atgaaacgca ttggactgac acaaagggta gatgtgattt    13350
ctaattatgg cgagagaaga gatgcaatag atcaaaaatg gtgctcgctt    13400
ttacttgaaa tgaatatgct acccatcccg cttcctaata tatcaccaag    13450
tattgccttt aaccttttg agcagcttag tctcgatggc gttatactta     13500
```

```
caggtggtaa cagtttaagt catttagatg ttttggcttc ggacctagct      13550
ccggaaagag atgcttttga actcgcctta attgagtatg ctttaaataa      13600
taaaattcct atatttggag tttgtagggg aatgcaaata attaactatt      13650
actttaaagg tgggtttgag ccgatagatg ggcatattgc aacgaatcat      13700
gctttagtca atttggatac taggtttaat ttaccagaaa atgtaaatag      13750
cttttcataaa tggggcattt cgaaagaatt attaggtgag aatttaattc     13800
caatagcaaa aaatattgat gatagtatag aggctattat tcacaaggag      13850
gaaaaaattg ccggaattat gtggcatcct gaacgtgtta aagattttaa      13900
tccattagat attaaattga tagaaaggat tttattgtga ctaaagctat      13950
aattttagcc gctggacaag gtacacgcct tcgacctatt acaaatgaca      14000
gaccaaaatg cttagtagag ctgaaaggta aatctttatt agaacggcag      14050
gtgaaaactt taaactcaca aggtatacat gatatacaag tagttacagg      14100
ttatttgtca gaaaaaatag aatctttggg ttataacact tcatttaatg      14150
cgcggtataa agaaagcaat atggttgaaa gtttgttttc tgcgattgag      14200
tttatcaaaa actgcaatga agatcttatc atcggatatg gtgatattat      14250
atatgatgag attaatttag aagcgctaat gaagtctgaa agtgaagtgt      14300
caataatgat agataaagag tggttagctt tatggtcatt acgtttagat      14350
aatcctttag atgacgctga aacacttgta atggataatg aaggttatat      14400
aacagagtta gggaagaaac cagagaatta cgcgcaaata caaggtcaat      14450
acacaggtct tataaaggta aaagcgggga aaataaaaga ttttatatcg      14500
ttttatgaag atctagaccg agaggttttg tatgataata aaaacttcga      14550
aaacatgtat atgactagtt ttattcaact gctaattaat agtggatgga      14600
aggttaaagc atctttggtt tgtaatggat ggctagaaat tgattcggtt      14650
gaagatctta tcatttatga gaaactagct gaaactgatg agttaaataa      14700
atttatatca ttatgaggat aaaggagggc tttccctccc ttatcgaagc      14750
ttagttaacc ttcattcaga gtatagtaac tgacctcatt gtaatacttg      14800
attttttattt aataaaatta ataactaaat cagcttcgca tactaccaat     14850
gttaactatt ttctagtcat atataaaaaa tagttgatag ctattacaca      14900
atgggtggtt atatatttct tcttagaata agcagttggc gaaatgtcct      14950
tagagtagtt gctatttaca cccctacttt cacgtgtctc tgctttcaag      15000
agtggtatga tgctaatgtg tttgtattat ttacgaaatg tttctagatt      15050
cttgttgaga gtctatatga atgaattact gtcaaaataa tgttcctctt      15100
taagtgttga ttgacaatca agagtcctaa aggatgtgta gaataagtag      15150
taaatgtatt ttgttgatag atgcaaatgg tcttgcattt gtatatgatg      15200
gtataaactt cctcattatt caacttgtac tgtaagccct tgatgcattt      15250
gagtctcatg ctcaaatata aaaccattgt atcaaatttt aaaggttgaa      15300
tagctccgcg gctacaagaa ctgcaattca ctttgagcta taaaactagt      15350
tcaaaaaaat tattgaaaag cttactgcta aattgtgcaa aaagcaggta      15400
ggtggttgag tactatattg tactagtctg ttaagataaa aatagaaatt      15450
tacaaaacaa tgctacattt ttcttttgga tttgtggcat agcataagtc      15500
```

```
ccatttaggg ttattattat aaatgctatt gatttttcta tgatgatcca    15550
agtaagtggt gttatgaaag aatcttgtat aattatgagt gtgtataaaa    15600
atgataattt ggaatatttg aaggatgcaa tcgatagtct attaaatcaa    15650
acatataata gttttcacat atgcatttgt aaagacggac ctttaccaaa    15700
agatattgat agtgtgttag aagaatataa taagaatatt gatgaattta    15750
cgttattatc caacaagaac aatgaaggat tagctaaatc actaaataaa    15800
ttgatagatt atgtaatgac cttcgatgaa gtgaaatata tagtacgtat    15850
ggatagtgat gacatatcaa gaaaaaatcg ccttgaaaga caaattgact    15900
atattaataa aaataaactt gatgtttgtg gtgcattttg cagagagttt    15950
ggtgctagtt attctatgga ccttaaggta gtccctttaa ccaacaaaga    16000
tattatagtt tcatctattg ataggtgtcc atttattcat ccgactgtaa    16050
tattcagaga tatagtatt  agaaatggat taaggtaccc ggaggatact    16100
tcatttactg aggatatggc tctttggtat aagattatcg aaagtggtta    16150
tataacagga aatatacctg aagtattgtt agattataga ttaaatgaag    16200
atacaataat tagacgtcta ggttgggcta aaggggttag tgagttttct    16250
attaggtata aatatataag agaaaaccat cttttatctg ttgtttcttt    16300
tcttaaagtc ttttctcgat tgttttttca tattcttcct gtacccatta    16350
taaaatactt atataagaat tttagataaa tatttattga tctttgttag    16400
aaagatattt tgcaacttgt tttaagtttg ttttttgttaa aatatattta    16450 atgtctttct cgaactgtga tgataaaatg agtgaaaata tttttaaaaa    16500
cacttactgg atgattattg ataaactggt tagtgttttc cttcttacat    16550
tagtcaactt ttttattatt agaacacttg ggcctgaact ttttggtact    16600
ttatcgtatg cccaaagttt cgtagcatta ttttttgtcta tatccttgtt    16650 tggtcttgaa gttgtaacta cgaagttgtt agtaaacagt gatatggcac    16700
ataaagcaaa tgtgattgtg aatagtcttt atataaggct aattgcaagc    16750
tttacttctt gtgttttaat taatttaacg tcctttatct atattcagga    16800
tgaatacaca agaaaaataa tattcatatt atctatttct ttgattttta    16850
atatgtctga catttttcta tattatttca actctctttc cttgtcatca    16900
aaaataattc cttataaaat aactgtaact attatcgtaa atgcaatgaa    16950
agtcggttta atttattctt cgcctaatgt tttaacattg tcatcattaa    17000
ttgtccttga atcaatgcta gtaatgtagt cttatgcttc cgtatttagg    17050
agtgagaaga taataaatgg ctttaatttt aacatcaata aaaaattgat    17100
aaggaatatt gctactgaag catggccatt gatattaagt ggagctatag    17150
taactgcata tatgaaaatg gatcaaataa tgattgacta tttcttaaat    17200
aaagagagag taggagttta tgcagcggct gttaaaataa gtgaggcttg    17250
gttttttatc cctatagctg tagcaagctc tacgtatcct ataataatta    17300
agtcaaagaa gaatcctgat ttgtatgaag agaaaatgaa aattttgtat    17350
tcgtgtaata tatggttgtc aatgtttgta ttttttgtttt tctttttac     17400 ttcagatttt atcataaatt tggttttgg aagtgaattt aatgattcgg    17450
```

```
tcaacgtttt gaagatatta gcctttgccg gagttatggt ctcgattggt      17500
gtaacaaata ccaattggtt aatgagtcaa ggattacaaa agataaactt      17550
aataaataag attattggtc taatgtttaa cttttttta aattataaat       17600 tgattcccaa atatgggata aacggtgcag ctatatccac cgtgatatca      17650
tatacgatta gtaatttctt agtgttgttg tctaactcta aaactagagt      17700
tagctttttt atgattttaa aatcattaga tgttagattg atatataaaa      17750
ttaaggaatt aaagaagtaa tgaagagtat tttaaagaaa gtgttaagat      17800
ggtcaattaa aaaatactat gcttatgtta gtagatatag gtattctaaa     17850
attgttaaaa aattaaaaaa taagaaaaaa attagcatta ccttttttgt      17900
tacttctgtt tcaaaatgga agtaccacga gttataccgc aagttgttgg     17950
acgaaagttt ttttgaagaa gtaaacgtat gtatcttacc tttgacccat      18000
attcaaaaag agctaagtga taaagagtat ctaaattgtg taaagtggtt      18050
caaaataaac ggttataaca aatcgaaag aaatgaaata aatgaacata      18100
cagatatagt ttttattct gatccttatg actttatcga aaacgatttt      18150
agaattgaaa atatgtcaaa acatttcttg tgttgttatt ctcaatactc      18200
ttatatggct ctaaatgctt atgaaggatt ttataatctt aattttcaca      18250
atatgctttg gcgatttttc tctgagtcta actaccattc gaatttgtca      18300
aagaagtatt gtggcaataa aggatctaat gtaatagtta gtggttatcc      18350
atactctgag attctactca aagaaactga aaatagcaaa ggagaaaata      18400
gacgtataaa atttcttta atttgggctc ctcatcacac tatcgaacaa      18450
gagaatggtc agcaaagcaa tttcttaaaa ttttcagata taatgcaaag      18500
tttttcagaa aaatataaag ataagataga ttttgtattt aaacctcatc      18550
ctaatcttaa atctagactt tataagtctg agcacctcgg atgggggaaa      18600
gcaaaaacag acgactatta tacatggtgg gattcccagg agaacacgca      18650
atgccatgaa ggtgaatata cgaaactatt ccaggaatca gatggactaa      18700
ttcatgattc tgcttcattt gttttttgaat atatgcttac aaagaagcca      18750
agtttatttc taatagataa aaaggtggaa caattagatt ttaatgaatt      18800
aggcaaaaaa gcggtcaaac gaagttatat cacaagtgat gcacatggga      18850
ttgagtcatt cattcagtca gtcataattg ataagtgtga ctataaaata      18900
gatggcagag ttgattttat ctttaatgac ttagacgttg atctatctaa      18950
cccaccatca aatgttataa ttaacgaatt aaaaagtgaa ttgtgctaat     19000
atgaataatt tggctcctgt tgtttattt acttataata gaccttggca      19050
tacaaaaaaa gtattagagg ctttggcaaa taatagtatt tctagttaca      19100
ttgacttgta cattaatatt gattcggctt ctaaagagac agatataaaa      19150
aaagttaaag aggttaaaga tattgtctac aattttagag gctttaaatc      19200
tattactgtt aatgaagcaa aggttaacct cggtgtcgat aattcggtta      19250
tttcttatgt atctgaggtt ctagaatctc atgatagggt tattgtgctt      19300
gaagatgatc atttaactaa cgaatcattt ctagaatata tgaatgctgc      19350
cttggatttt tatgaaaatg atgatcgtat tgaaggtata agtggattct      19400
cgccaccttt aaactggagt aacttaaata cgagtaatga tatttatttt      19450
```

```
gctccaaggg gatcttcctg gggatgggca acatggagaa aacggtggaa      19500
tgcaattgat tgggaaatga aaaaatatcc tgaatataaa tcttgtaaga      19550
acaactatgc gcattttcc gatggggaa atgatttgcc tttgatgtta       19600
aagacggcga tggagttaga agttactcct tattgggata taaggcggtg      19650
ctttcacatg atgctcgaga ggagttattt tgtttatcct agatttagtt     19700
acgtaaaaaa catagggctt gatggcacag ggttacattg tggggaatct     19750
gaacgttata tggttagctt gaagaaagaa gctattggtt tgccaaattt     19800
taaatccttt aaaattgatg atgatgtgtt aaccgagttt agaaaagtgc     19850
atcaaataaa tttatttaaa gcccacatcg cttttttatt acgtaaactt     19900
cacctaaagt aggaaaaaca atgaatccat tgattttatc tcactctgat    19950
agtattggtg gcgccgcaag agctgcttat agaattcatt cagaacttat    20000
tcttaacaat atcgaatcta agatgatggt tagagttaag atgcttgatg    20050
atgatactat tttgggacca accaatgaat tgacaatag agtttgtcaa    20100
atgagaacta agtttaattc tgtattaaat aaggtgcttc catttagaac    20150
ttcctatcaa tccttaatc ttttgccatc gaatcttaat ggagttataa     20200
atagtagtaa ctattcttta gttaattttc attgggttgg cgctgaaact    20250
ataaattttg aagatgcaat taaattaat aagccgattg tatggaccat     20300
gcatgacatg tggcctgtgt taaatggatc tcatataaca agtgctacta    20350
gttattccca atggaaggct agttcttctt ccatttcaaa cttttttaaac   20400
agtaagaaat ggagtttctt agaaaagtta gaccacgtag tgactcctag    20450
tttttggttg gctgatttta taagtcaatg tccttcgtta tccaataaac    20500
caatatcagt tatccccaat gtcttagata tggatgtttt taagccaaag    20550
atgaaacttg atgctagaaa gttgcttggg ttgaattcag aaaaagtatg    20600
tttactcttt agtgcaaatg gtggaactcg agatttcaac aagggctttg    20650
atatacttaa agatgcatta aatatggtct ccactacatt gggcagagac    20700
aagtttgagt tgataattgt tggtcaacac gaacctgttg ggtttaaaat    20750
gccatgtgag accaaatggt tcggtcatgt ttctgacgat gatttttggg    20800
cgactatata cgccgctgtc gattatacta ttattccatc gagaatagaa    20850
aactttccac aagtaggaac tgagtcgatt tgttctggaa caccattaat    20900
cggtatgcct acgacgggtg ttaaggaatt aattggtgat tctgagagag    20950
ggttagttgc taatcgtgtt tgtgctacct ctttggctga ggtaataaag    21000
gttgcaatat atgaaaggaa tatttttagt caagaggttt taagaaaata   21050
cgcgttggat aactggtctt ctgatatagt ttacaccaaa tacaaaacag    21100
tatatgaaaa tgtttaatct ttcagtcact ttttttaaaa ctctaatttt    21150
atctttttct ttttttatta taggtattta tgcatattta aatggtgggt   21200
tttatcaaaa attagaattg gatgttttca tttattctgc gatagatatt    21250
tttttactt gcatagttgt ttctttattt gtaaataaac gctatgcaag     21300
agagttgtca gagttaagct cgttttttga aattaataaa aataaattat    21350
ttctaatttt tgtacttctc gctattatcc cagtttttta ttcaatccat    21400
```

```
tctataaatc acttttatc tggaggaatt aaggaggagt taaagtttcc         21450
tgcatttatt agtatttata tgatgttttt ttcaacttta acgaaagttt        21500
tattcccaat ttcggttgca ttaaaatcat caaaaagata tgtaatggca        21550
ccattgtttt tttgcttatt tttatcattg tcttttggag gatcgacggc        21600
cgagttacta tttgtaatgt ttagttttgt agttctctcc ctgatgtaca        21650
aattgttgcc tattaataaa ataattttat taatagtcag tttgttttca        21700
tttgctgttt tgatttctgc acttgtacag tctagtcgat atggaggaaa        21750
tttgtttgct taccttttca agttgtttat gaagttagcc acatatagaa        21800 gttttttcatt ttatcttgca gactatgtaa atcagcttga aagctactat       21850
atgatacttt acccttttct tgggtatgga gcaggaaaat ttaatgaaat        21900 ttttttcttct tcagctaact tatataataa tgaatttgtt atggtataca       21950
ggaatatagg cttttttaat ggtaattatt acttagcaaa tgttatatac        22000
ccatggtgga gtttcttctt tcaatctttt ggtattattg gcttgtttat        22050
aaagccagtt tatttgtttt ttattttttaa agttgttact ttatttaggc       22100
ttcgggtgac gttgttttttt ttaattgtgt ataatatatt tttagcacag       22150
caaactcata tgcttttaac tattaacagt tatgtcttgt ttttttctct        22200
tatagttttt gatttgattg tgaataatgg gttgaggaag gtgaactaaa        22250
tggattttat atcaatcgtc actgttaact ttaacgactc taacggttta        22300
aaaaaaacgt tagagtctat tactaagcag aagagttttt gtaaatcttt        22350
ggttcaactt attgttattg atggcggatc taatgatggc agtttagaag        22400
ttatacacaa ttataaggat gcgctttcaa tagtattaag tgaaccagat        22450
gaaggcatct atgacgcaat gaataagggg ttagagtatt gtagagggac        22500
gcatgtattg ttttttaaact ccggtgacta ttttttgtact gacaatgcac      22550 tgacggtctt atatgaacaa ataagaatac gcactgatag tgttattttt        22600
tggcccgtgt cagttgtcag tgacaaaact agttggtatt acccaaatgt        22650
ttcaaaactt gacataccta gttggctcaa aaaacacctt ccaaatcatc        22700
aagctatgtt atttccaagg tcttttctaca ataagaataa atatgattta       22750
tctatcccaa tatcttcaga tgcagattat aaaattagaa gcttgagtta        22800
caatgattac tttatcttg attctcctct tactgctttt gttcttggcg         22850
gggtatccag taaacctctg ggttttaatc ggtatatgtt gctgattcga        22900
gattcaaaca tgcttaataa taagcactat aatgggttct tattatttaa        22950
gactaaagcg gttttttttac ttaagctaac cgtaaagctt gttattagta       23000
ttttttttag aagtggtttt tattacagag tcttgtctat tattaataag        23050
agaagatgat gttatattaa gttttatttg tagcgattta actctctgat        23100 ttttttaaaga atgaaaataa aataatttaa ttttgttcat aatgtatgag       23150 tttgattttta atttttatgt ttaatattat tgataggtaa tataacaagt       23200
gggatttatg aaaaaagcat taattactgg tattacaggt caagacggct        23250
cttatttagc agaacttcta gttggaaaag gctatgaagt tcacggtctt        23300
attcgtcgag catcatcata caatacggag cgtattgatg cgttagtaaa        23350
cgcaggggct aatgtcaaat tacattacgg tgatctaacg gattcttcaa        23400
```

```
acttgattcg attggttaaa gaaattcaac ctgatgaaat ctataactta        23450
ggtgccatgt cgcatgtagc ggtttctttc gaatctccag agtatgtcgc        23500
tgatgtcgat ggcatgggta ctctccgtct tctagaggcg attcgtatca        23550
acggtttgga aaagaaaact cgcttttatc aagcgtcaac atctgaactt        23600
tatggcgaag tccgagaaat tccacagcgt gaaacgacgc ctttttaccc        23650
acgttctcca tacgctgtgg ctaaaatgta cgcatactgg attgtggtta        23700
actatcgtga atcttacggt atgtacgcat gtaatggtat tttatttaac        23750
catgagtcac cacgccgtgg tgaaaccttc gtaactcgaa agattactcg        23800
agctatcgct aacatctctc aaggtctgga atcttgccta gaacttggca        23850
atatggatgc gttgcgtgac tgggggcatg ctaaagatta cgttcgaatg        23900
caatggatga tgcttcaaca agagcaggct gaagattttg ttatcgctac        23950
tggtaagcag atctctgtgc gcgagtttgt tcgcttgtca gcgaaggaag        24000
cggggatcga acttgagttt tctggcgaag gaattgatga aatcgctact        24050
gtggttgcta ttgatgaaga aaaggcacca aaagtgaaag ttggtgatgt        24100
cattgtaaaa gtaaaccctc gcttcttccg tcctgctgaa gtagagacat        24150
tacttggtga cccaagtaaa gcaaaagcta aacttggctg gactccagag        24200
atcactgtag aagaaatgtg tgcagaaatg gttgcgtctg atatcgataa        24250
ggcaaaacaa cacgcggttc taaaagaaca cggatttgac gttgcgatct        24300
cattagaaag ctaattaatc agtaatactg attcgtttat attgcagagt        24350
tcctcatttt gggctctgct ttttctattt atattatcgg aactagtatg        24400
aaaagagtat ttgtcgctgg tcataaaggt atggttggct cagctattgt        24450
tcgtcaacta tctaaagact cttcagtaga agttattact aaagatcgta        24500
atgagctcaa cctgttagat gcactagccg tcgagacgtt ttttgcgact        24550
cacaatattg atcaagttta ccttgcggcc gcgaaagttg gtggaattgt        24600
tgctaacaat acgtaccctg ctgagtttat ctaccaaaat ttgacgattc        24650
aaaacaatat tattcactct gcacatctgc atggtgttca agatttacta        24700
ttcttggggt cgtcttgtat ttatccaaag tttgcacaac aaccgatgcg        24750
tgaagactct ttattgactg gaactttgga agaaaccaat gagccttacg        24800
caattgctaa gattgcaggt atcaaaatgt gcgagtccta taatcgccaa        24850
tatggttgca actatcgatc agtaatgcca actaatttgt atggtgaaaa        24900
tgataatttt catcctcaaa actcccacgt tattcccgca ttgttgcgtc        24950
gctttcacga agcaaaattg aatggcgaca gtaaggttgt tgcgtggggg        25000
agcggtaaac ctatgcgaga gttttttacat gtagatgata tggcagcagc        25050
ttcaatttac gtaatgaatc ttgctcaaga ggtgtatcta gaaaatacgc        25100
aagaaatgct tagtcacata aacgtaggta caggtgtgga ttgtactatc        25150
cgtgaacttg ttgaaactgt tgcaaaagtg gttggctttg atggcgaaat        25200
tgaatttgac actacgaaac cagacggcac tcctcgtaag ttaatggatg        25250
tttcacgttt aaagagtctt ggctgggaag cgaagacgag cctagaagat        25300
ggcttaacta tgacttacca gtggttccta gagaatcaag aaaactatcg        25350
```

| | |
|---|---|
| cggttaaagt acctagggta gagctaatat tagggggttaa acaaagcata | 25400 |
| tgttttttaag caaacaacgt ttttctcaag tgattgaaag tacgccatta | 25450 |
| gtttcaattg acttagttat tgaggacgaa agtggtcaag ttttacttgg | 25500 |
| agagcgttta aatcgaccag ctcaaggttt ctggttcgtt cctggtggtc | 25550 |
| gtattcttaa agatgaaaag cttgaagatg cctttgctcg tttaactttg | 25600 |
| gaggagcttg acatgagtt taagctctct caagcaacac tgatgggacc | 25650 |
| ttatacacac ctctatgatg acaatgtatt tggcaatgag tttacgactc | 25700 |
| attatgtcgc gattgcctac aagctcattg tcattcgctc tgaattgaac | 25750 |
| ttacccatgg atgtacagca ttctcgttac cgttggtgtc atcaagatga | 25800 |
| attattgacc agtgataaag tacatattca tactaaatgg tattttcaaa | 25850 |
| aataactaaa actatcacct aattaaaaac aacgagttga ctatgcttat | 25900 |
| tcctgtaatt atggccggcg gctcaggcag tcgtttatgg cctctatctc | 25950 |
| gttcaaaata tcctaaacaa ttccttgcag taactggtga acaaaccatg | 26000 |
| cttcaacaaa cgttgagccg tatggttggt ctagaacaca atgcgccgtt | 26050 |
| tgttatctgc aatgaagaac atcgattcct agttgctgaa cagcttcgcc | 26100 |
| gtattaatgg caatcatagc ggaatactct tagagccagt agggcgtaat | 26150 |
| actgctcccg ctatcgctct agcagcaaaa tttgccctat ctgaaaatca | 26200 |
| aacttcaggt gaagatgctt tgatgttagt tcttgctgct gatcatgtga | 26250 |
| ttaaagatac tcaatctttc catcagtcgg tgcaagctgc tattccgtac | 26300 |
| gcacaacgtg gtgatatggt cactttcggt atcaaagcga atgcaccaga | 26350 |
| aacaggttat ggctacatta aaaccggtgc tacggttact gctgcggatg | 26400 |
| agagtcgagg ctttagtgtt gatagctttg ttgaaaagcc tgatctcgaa | 26450 |
| accgcaaagc aatatctaga tgatggtagc tacttgtgga acagtggtat | 26500 |
| gttttttattc aaagcatcta cttatcttga agagttagca aagttccgac | 26550 |
| cagatatctt gaaagcatgt gaaagtgctt acgatagtca ttttgacgat | 26600 |
| ctagacttta ttcgcatgtc atccgaacta ttctcacaaa tcccagacga | 26650 |
| atcaatagat ttcgccgtaa tggaaaaaac agaaaaagct gttgttgttc | 26700 |
| caatggacgc aaattggagt gatgttggtt cttggtcggc actctgggat | 26750 |
| gtgaatgata aagatgagca gggcaatgca attcgcggtg atgtcttaac | 26800 |
| tgagcaaact cggaatagtt atgtttattc acaagataaa ctcgttgcta | 26850 |
| ccgttggtat tgaaaatcta atcgttgtag atacgaaaga tgcagtgcta | 26900 |
| gttgcgaata aagacaaggt tcaagatgta aagtcgattg ttaatcaact | 26950 |
| aaaacaacaa aaccgagcag agtgtcagca gcatcaagag gtatatcgtc | 27000 |
| cgtggggttc tcatgagacg gtatctgaag gtgagcgtta ccatgtgaaa | 27050 |
| caagtgttag ttaagccaaa agagaagact gctctccaga tgcaccacca | 27100 |
| tcgagctgag cattgggttg tcgtgtcagg tacggctaaa gtgacaaaag | 27150 |
| gtgatgaaac tttccttctt actgaaaatc agtcaactta tattccagta | 27200 |
| gggactccgc actctgtaga aaatccagga caagtgcctt tggagcttat | 27250 |
| tgaagttcgt tctggatcgt acttagaaga agacgatatt gttcgctttg | 27300 |
| atgagcaagc atctaagttt ggtggtgact actaactact tattgagata | 27350 |

```
ggaattatgg taacaaaatt aatcagtagt gaagtgcttg gtgcttcagg        27400
cgttcagttt ggtactagtg gcgcgcgagg actcgttact cagtttacac        27450
cggacgtctg tgctgcattt actcacgcat ttttggcatc aatgcgtcgc        27500
aattttactt tcaatcaaat ggctgtggca attgacaacc gccctagcag        27550
cccagcaatg gcaaaagcag tcattcaagc gcttactgat tcaggtattg        27600
acgccgttta ctatggtgtt gtacccactc ccgctctagc ttttaccgca        27650
atgcaagaca atatgccttg catcatggtg actgggtctc atatcccatt        27700
tgaccgcaat ggaattaagt tctatcgccc ggatggagag atcactaaag        27750
cagatgaaca agcaatctta accgagaagg tagactttag tgctatcaat        27800
gacctgcctg agttaacgat taatttccgt gcggcagagc tttaccgagc        27850
acgttatacc gatttgtttg atgcagattt actggcaggg aagcgtgttg        27900
gtatatatga gcattcaagt gccgggagag atatttacca aggactttt        27950 gaatcgcttg ggctgaagt catatcattg gagcgtactg atgagtttgt         28000
tcctattgac actgaagccg ttgctgaatc tgataaggaa aaagcacgca        28050
gttggtcgaa gaaatataat ttggatttta tattttcgac tgatggagac        28100
ggtgatcgtc ctttagttgc tgatgagagc ggcgaatggt tgagaggtga        28150
tatcctaggc ttactttgtt cgcaagcgct tcaagtcgat gcattagcag        28200
ttcctgttag ttgcaatact attattgctg aatcccctga atttaaagcc        28250
gtatctaaaa cacgaattgg ctcgccttat gttatcgctg aattttccga        28300
attagcaaaa acttataaaa gaattgcagg gtttgaagct aacggaggat        28350
atttgctcgg gagtaacatt ttggtgaatg ggaaatctct aaaagcactg        28400
ccaacccgag atgctgtttt acctgcgctt atgctgctct ctttagcgaa        28450
aacatcatca atcaaaagct tggtaagcaa tctcccacag cgctttacgc        28500
atagtgaccg tattcaaaac tttcctacgg agaaaagttt agcaatactt        28550
gagcatggca agatgaatcc tgaagaatta ctgctaaagc ttggctttac        28600
ggacttaaaa gtagaaagca ttaacactac tgatggtttg agattgtctt        28650
tgactaatga tgtgatcatt cacctacgac cttctggtaa tgctccagaa        28700
ttacggtgct atgctgaagc tgcgtccttt gatacagcta aagcgcttgt        28750
aaactctgtt ttgttgcgtg tgcagcaact ttaataaaaa taaaaatat         28800 aaaagcttga cttggaataa tctaagtcaa gcttttttcg tttaatggta        28850
atgctgatga actttttaa actaaataac ccaatacaaa attatgcatg         28900
gggcagtgag actgctcttc aagagttgtt tggaattgaa aatccaaacc        28950
aggaacctca agcagagatt tggatggggg cacaccctaa cggatgctca        29000
aaggttcaac ttgaaggtga agagtttctt ctatctgagt ttattgctaa        29050
agataaagct aaaattttat cgaccagtac agagcaaaaa tttggaacgc        29100
taccctattt gtttaagata ttgtctgctg ggaatgcatt atccatccag        29150
gtgcatccaa ataaattgga agctgagcaa gggtttgcta agaggaaga         29200 gttagggctt gagcttctg cgccaaatcg caattataaa gatgcaaatc         29250
ataaaccaga gttggtatac gctttgactc cataccaagc tatgaatggc        29300
```

```
ttccgcgcat ataccgagat tgtcttgctc ttctcaaaag ttatagaaga         29350
atccaatgta cctgtaattc accagctgtt ggaagccttt aagaaaaact         29400
taacagctac aggtttagaa gctttctta ttgggatctt atctttagag          29450
ggggaagcga aagaagcatc tattcaaggg ttaattgagt atgcaaaagc         29500
atatcagcag ccgagtatta aaaatgattt aggaactcta attgtggagc         29550
taaacaaatc ttaccctggt gatattggtc ttttgctcc tcttatgcta          29600 aatgttttga cgctttctcc tggagaggca atgttccttg atgcaagaac         29650
accacatgct tatctaaaag gtactggctt agagataatg gcgaattcag         29700
ataatgttct ccgggctggt ctaactccaa agcatattga cgtggtagag         29750
ttagctcgtt gtactttgtt tgaagagaag tcatcagact ctctattgct         29800
cacaccagaa gttttgggga ataggttgag ttattcagtg cctgtttcag         29850
attttaaatt tgactgtctc atgaaatcga acgacgagaa ggttgtaatg         29900
caaagcgctg aaatattact tgctatcgat agttcgttaa cgctatatca         29950
tgcttctggt gaaactttaa cgttaggtag aggtgagtcg gtgtttattc         30000
ctgcatacgt aaaagagtat tcaatcaatt caaagggaag ggtcgcgaga         30050
gcgtataact gatataggta tggctaagtg accaccaagc aagagcattt         30100
ctggtcactt agctgcatgt tttaggttat agggttccag attgctgaac         30150
gctagttgtc ttatttagtt ttgtccttaa gaagctagta attttccaaa         30200
tatacgccaa aatgattgag taaattacaa agcacgaaat gaataaaacg         30250
aacatcgtta cttctgaaat atttgtagcc tcaccataaa tcccgaaacc         30300
agcgtaaagg cttgcaataa agcatattgc tacaagagtt tgttttggtc         30350
caagccctag acgttggaag atatgatgca aatgttcacg atctggtttg         30400
aatggagagt cgcctctgcg aatgcggcga atcattattg cggccatatc         30450
cattaagggc acggcaatca gccaaagagc ggttactggt cgcattagtg         30500
gttcagaact tccagtttgg ctaactccta gcagcaacca aatcacagta         30550
aagccaatca tcatactacc agcatcaccc ataaatactt ttcgctctct         30600
ccctagtatc ccaaggttca taagatata aggaagcata gctacaatga          30650
tgactacaca taaataagct agaccatgtt ggctatcaac ttgcaataaa         30700
aatgctagtg caccgaatgt tacaatagaa agaccgccta gcaagccgtc         30750
gataccatct accatgttaa aggcattaat agcaccgatt actgctacta         30800
tagtaattaa actgcctgcc caacctaaag acacttctcc aatcccaaac         30850
atatctccga gattattaag ctcaagcccc gcaactttca tcataacaat         30900
cgacaaaatt gcttgaatcc ctaagcgaac tttaaagcta aggtcagttt         30950
tgtcatcaac tgctccaact atcgtaagta cacaaatgca cagtaagtag         31000
agccagctgt gttcaatagt atctgggttg aaggttagat attgcgctag         31050
tactaaacaa atcgaaagac ctccaactaa agggactgct ccgttatgta         31100
atttacgagc gttgggttg tcgaccaaac cgattcgttt tgcaacttt           31150 cgcattaaga agagcgttgc aaaagaagag aaaaagataa aactgagttc         31200
aaggaacata aaatagccaa ctgtgatttt acatataatc gcctaatttt         31250
agctcaagtt ggtggtatga aaaagttact gttcaataaa aaatataagt         31300
```

| | |
|---|---|
| tgttgtgtca aataaggtcg tttgaatcaa tgccacgtgc gatgacgtag | 31350 |
| tattcttgat atcctaaaga aaatgaggtt ttagggtttg ttcatgaaaa | 31400 |
| ttgctgtcgc tggtaccggc tatgttgggc tttctaacgc tatgttgtta | 31450 |
| gctcaaaacc atgaagtggt tgcactagat attgttcctg aaaaagttga | 31500 |
| attgctaaac aaaaaacaat ctccaattgt tgatgctgag attgaacact | 31550 |
| tccttgaaaa cagggaacta aacttcatcg caacaaccga taagcagaaa | 31600 |
| gcttatcaag gtgcagaata tgttgtgatc gcaacgccaa cggattatga | 31650 |
| ctcagtcacg cattacttta atacttcttc tgttgaagcg gtgattaaag | 31700 |
| atgttatgtc catcaatcct gatgcagtaa tggtgattaa gtctactgtt | 31750 |
| cctgttggct atactgctcg aatcaaggaa gagtttgggat gtgagaatgt | 31800 |
| catcttctcc cctgagttct tgcgagaggg caaagcgctt tatgataacc | 31850 |
| ttcacccatc acgtatcatc gttggtgaac gcagcgaacg tgccgaagta | 31900 |
| tttgctagct tgctagtgga aggagcagta aaagacgata ttcaagttct | 31950 |
| atttactgac tctacagaag ctgaagcagt caaactgttt tcaaacactt | 32000 |
| accttgctat gcgtgttgcg tacttcaatg agctggattc ttacgcagaa | 32050 |
| gctcatggct tggatgctcg tcagatcatt gaaggtgttg gtttagatcc | 32100 |
| tcgtatcggt aatcattaca caacccatc atttggttac ggtggttact | 32150 |
| gcttaccaaa agatactaag cagcttttag ccaattacca agatgtacca | 32200 |
| aacaacatca ttggtgcgat tgttgatgct aaccgtactc gtaaagattt | 32250 |
| tgtggctgaa gctattctta agcgcgaacc aaaagttgtc ggtatttatc | 32300 |
| gtttaatcat gaaggcgggc tctgataact tccgtgcttc ttctattcag | 32350 |
| ggcatcatga agcgtatcaa ggcgaaaggt gttgaggtcg tggtttatga | 32400 |
| acctgtactc aaagaagaat atttcttcaa ctctcgagtg attgaagatc | 32450 |
| tgagtgaatt caagcaaagt gcagatgtga ttgtttccaa ccgcatggtg | 32500 |
| gaagagttag ctgacgttgc ggataaagtt tacacgcgtg acttgtttgg | 32550 |
| tagtgattaa atttttagta taacgataat atatggctct catgcatgag | 32600 |
| ggccttttt acagttggtg aatttaaaat gattaaaaaa tgtctatttc | 32650 |
| ctgcagcagg ttatggtacc cgcttcctac ctgcaacaaa atctatgccg | 32700 |
| aaagaaatga tgccggttgt caacaaacca ttgattgaat atggtgttga | 32750 |
| ggaagcgata gaagcgggca tggatggcat gtgcattgtc actggtcgtg | 32800 |
| gtaagcactc tttgatggac cacttcgata aaaactatga gttggagcat | 32850 |
| caaatttcag gaacaagcaa agaagcactg ttggacgata tccgttcttt | 32900 |
| gattgattca gcgagttaca catacatccg tcaacgtgag atgaaaggtc | 32950 |
| ttggtcatgc tatcttgact ggtcgtgagt tggtgggtga tgagccattt | 33000 |
| gctgttgtac tagcagatga cctttgtgtg aatgaagagc agggcgtatt | 33050 |
| agcgcaaatg gttgagcttt acaagcagtt ccgttgttct attgttgcgg | 33100 |
| ttcaagaagt tccagaaact gagacccata gtatggtgt gattgctgga | 33150 |
| gagatgatca agatgacat cttccgaatt gataatatgg tagaaaagcc | 33200 |
| agaaccaggc acagcaccaa gtaacttagc aattattggt cgctatatct | 33250 |

```
taacgccaga tatttttgat cttatcgaaa atacggaacc aggcaaaggt      33300
ggagaaatcc aaattactga cgcattgatg caacaagcgc aatctggttg      33350
tgttattgct tacaaattta aaggtcagcg ttttgactgc ggcagtgtag      33400
aaggttacat cgaggcgaca aactactgct acgagaacct atacaaaaaa      33450
gcgtctagtg ctgagcttgc taaaacacca actgtaaagg ttgctgaaac      33500
tgcatagttg ttcggtctcg ttaccaatgt gctttaacat ggctttctga      33550
cgtacaaagc ttagttaaag cacgttgata tccaaattct tatgctgttt      33600
taactgatta ataataagca agaactaggt tatatcgttc taatgtcggc      33650
tgatattagt ttaataaacc acctcaattc cctctgcttc taacttctct      33700
cctaactctt ttttacttct ttctctccat gtatcaaatg cacggctttt      33750
ggttgtactg gaataccaat aacaaacttc aataaatcgc tttggtctgc      33800
gtgtgcagaa tatccagaga tggtatggaa ctgtgcgttg gcttcgattg      33850
gttggttatc gatatccacc gtgtggctgc ctgattggat ttctcgccct      33900
aaggttcctt gcgcttgata gcccgcaaac aacacatcat ttcttccgtc      33950
tggcaagagt gcttttaagt aattgacgat tcttcctcct tcgcacatac      34000
cggatgccgc gacgacaatt gcaggctcat cggtggaggc tagtcgattc      34050
actaatgctt gatgttctcg atggttttct acagtaatgc attgttcaaa      34100
agcgagggga tgacgatgat tgttgagctt ttgctttgct tcttttccct      34150 acagttttt gaaacggcgg taggtcttcg tgactctttt cgcaagcggt       34200
gagtctagga taattggcaa agaagacgac aagtcgcgtt ggtgaatcag      34250
ctgttcaata tcgaataaca gttcctgcgt acgtcctacg ctgaaagctg      34300
ggatcagaat aacaccaccg tcttgcagtg cgtgatcgat aatggcgttc      34350
aagcgctcag ttcgagtggc aatgtcttta tgttctttgt tgccgtatgt      34400
ggactctatg aacagatagt cggcacgctt tggaggtttt ggatcgggta      34450
agagcggggt attggacgga cctagatcgc cggaaaacac gatgatttca      34500
tgattgggga gtttgaattc tacgtaagcg gaaccaagaa tgtgccccc      34550 atgttggatg tgcagaggga taaggtttct aatgtcacat acgttttta      34600 gagtgacaga attcacaggg tagttctcag gcaaacaaaa agggatgcat      34650
gatgcacccc tttgttattt ttactgagag taaaaacgag attacgcttt      34700
tgctttagcc gctgctttag cgattgctgc gaaacttttc gcgtctagag      34750
aagcaccgcc aacgagagcg ccgtcgatgt ctggttgtga gaagtaagct      34800
tcagcgtttt ctggcttaac agaaccaccg tattggatga ttacttgtgc      34850
tgcaactgct tcgtctttcg ctgcgattag tgcgcggata gaagcgtgga      34900
tgcgttgtgc atcttcagct gttgctgctt taccagtacc gatagcccag      34950
attggttcgt aagcgatgat tgcgccgttt agagcttcaa caccgtaagt      35000
gtcgataact gcgttgattt ggcgtgcgca tacagcttca gtttcgccag      35050
cttcgttttg agcttcagat tcaccgatac agaaaacagg agttagactg      35100
ttttctttta ggaagttgaa tttcttagcg atgaactcgt cagattcgtt      35150
gtggtattca cgacgctctg agtgaccgat gatgatgtga gaagcaccga      35200
agtctttcag catttctgga gacatgtcgc cagtgaaagc accgctgtta      35250
```

-continued

| | |
|---|---|
| tttaggtcag tgttttgagc acctaggatg atcttgttac cgccctcaac | 35300 |
| aattagacgc tcagccagat ctaggtaaag tgcaggtgga gctactgcta | 35350 |
| cgtcaacacc ttcaacgcct tcaagctcag cgttaagacc agttagcagc | 35400 |
| tcagttacca ttgctttgct gccgtttagt ttccagttac ccatcactac | 35450 |
| aggacgacgc at | 35462 |

METHOD FOR PREPARING A K SERUM WITH A VIBRIO PARAHAEMOLYTICUS AS AN ANTIGEN

BACKGROUND OF THE INVENTION

Technical Field of the Invention

The present invention relates to the field of biotechnology, in particular to a novel K-serotype of *Vibrio Parahaemolyticus* and an application thereof.

Description of Related Art

*Vibrio parahaemolyticus* (VP) is the main pathogen of foodborne diseases. Humans are mainly infected with it by seawater exposure or eating raw or undercooked seafood. It usually causes acute gastroenteritis, and occasionally wound infection and sepsis. In severe cases, it can cause death. In China, data from the Foodborne Disease Outbreak Surveillance Network show that foodborne diseases caused by *Vibrio parahaemolyticus* have surpassed those caused by *Salmonella* and *Staphylococcus aureus*, and *Vibrio parahaemolyticus* is becoming the major biological pathogenic factor in foodborne disease outbreaks.

Serotyping is commonly used in the source tracking and genetic variation studies of bacteria. *Vibrio parahaemolyticus* can be serotyped based on thermostable somatic (O) antigens and thermolabile capsular (K) antigens. At present, the Japanese *V. parahaemolyticus* Typing Committee has identified 11 O serotypes and 69 K serotypes. Prior to 1996, *Vibrio parahaemolyticus* infections did not present a clear dominant serotype until February 1996, when a new O3:K6 serotype strain caused a mass outbreak of food poisoning in Kolkata, India. This new strain subsequently spread widely across continents in populations in many coastal countries and regions around the world, and led to many large-scale outbreaks, becoming the major subspecies of *Vibrio parahaemolyticus* pathogens. However, since 2013, a new type of *Vibrio parahaemolyticus* that agglutinates with O4 serum but does not agglutinate with the existing 69 kinds of K sera (KUT) has increased significantly, leading to a predominant spread of infection across regions and populations in a short term. It is very likely to become an important epidemic strain. Genome sequencing revealed that the sequence of K epitope of this new strain is different from those in the NCBI database. It is therefore considered that this *Vibrio parahaemolyticus* strain is a novel K serotype strain, named O4:KUT-recAin. It was deposited at the China General Microbiological Culture Collection Center (CGMCC for short) with a deposit number of CGMCC No. 17249 on Feb. 20, 2019. After relevant articles are published, the materials required are to be submitted to the *Vibrio parahaemolyticus* Serotyping Committee (Japan) to name the new serotype. The present invention relates to a novel K (capsular antigen) serum for *Vibrio parahaemolyticus* and a preparation method thereof. The prepared serum can be used to effectively diagnose and monitor the outbreak of this serotype of *Vibrio parahaemolyticus*, and it is of important significance for the prevention and control of infectious diarrhea pathogens.

SUMMARY OF THE INVENTION

The objective of the present invention is to provide a novel K (capsular antigen) serotype of *Vibrio parahaemolyticus* and an application thereof.

The technical solution adopted by the present invention is:

A *Vibrio parahaemolyticus* with a deposit number of CGMCC No. 17249, named *Vibrio parahaemolyticus* O4:KUT-recAin strain.

The *Vibrio parahaemolyticus* O4:KUT-recAin strain provided by the present invention was deposited at the China General Microbiological Culture Collection Center (Institute of Microbiology, Chinese Academy of Sciences, No. 3, Yard 1, Beichen West Road, Chaoyang District, Beijing) on Feb. 20, 2019, with a deposit number of CGMCC No. 17249, classified as *Vibrio parahaemolyticus* as proposed by the deposit center. The deposit center identified the strain as alive on Feb. 20, 2019.

Application of the above *Vibrio parahaemolyticus* in the detection of diarrhea-associated pathogens.

The preferred application involves serum.

A serum, wherein the serum is a specific immune serum prepared by immunizing an animal with the above *Vibrio parahaemolyticus* as an antigen and through adsorption.

Preferably, the antigen is an inactivated antigen.

Preferably, the animal is a New Zealand white rabbit.

Preferably, the serum achieves specificity through adsorption with other different K serotype strains.

The specific steps are as follows:

(1) Preparation of Antigen:

*Vibrio parahaemolyticus* O4:KUT-recAin strain was seeded into a BHI medium with 3% NaCl and cultured at 37° C. overnight. The bacteria are collected, washed twice with normal saline, and then inactivated with normal saline containing 0.5% formaldehyde for 24 h. The inactivated bacteria are then dissolved in normal saline to act as an antigen.

(2) Collection of Immune Serum:

Healthy 12-week-old New Zealand white rabbits are selected. The inactivated *Vibrio parahaemolyticus* O4:KUT-recAin strain is dissolved in 0.85% NaCl at a concentration of 109 CFU/ml, and injected into 4 sites of each rabbit's back for immunization, 250 µl for each site. The immunization is boosted once every two weeks in an immunization volume the same as the first immunization, 5 times in total. Thereafter, whole blood is collected from the heart. The collected whole blood is left at 37° C. for 2 h, transferred to 4° C. overnight, and then centrifuged to collect serum, which is the immune serum.

(3) Preparation of Specific Immune Serum:

The resultant immune serum is subjected to agglutination reaction with *Vibrio parahaemolyticus* O4:KUT-recAin strain, and it shows that agglutination is obvious and there are cross-reactions with K24, K59, K61 serotype strains among the known K serotype strains. The immune serum is sequentially adsorbed with K24 strain, K61 strain, and K59 strain at a concentration of 109 CFU/ml inactivated with 0.5% formaldehyde at 4° C., and then centrifuged to obtain a supernatant which is the immune serum specific to the *Vibrio parahaemolyticus* O4:KUT-recAin strain, also referred to as a novel K serum in the present invention.

(4) Properties of the Novel K Serum:

The novel K serum agglutinate with the *Vibrio parahaemolyticus* O4:KUT-recAin strain obviously. It does not agglutinate with 33 known K serotypes of *Vibrio parahaemolyticus*, not with other intestinal pathogens *Vibrio cholerae*, *Vibrio fluvialis*, *Campylobacter jejuni*, *Campylobacter coli*, *Escherichia coli*, *Salmonella typhimurium*, *Salmonella typhi*, *Shigella dysenteriae*, and *Shigella flexneri* either. After diluted 64-fold with normal saline, the novel K serum still agglutinates with the *Vibrio parahaemolyticus* O4:KUT-recAin strain obviously. The novel K serum has good specificity and sensitivity.

Advantages and Effects of the Present Invention:

The advantage of the present invention is that it provides a novel K (capsular antigen) serotype of *Vibrio parahaemolyticus*, which is used to prepare a serum specific thereto for the detection of pathogens related to diarrhea. The prepared novel K serum is highly specific, and can be used to conveniently and quickly detect a novel K serotype of *Vibrio parahaemolyticus* (O4:KUT-recAin) which has a rising infection rate in recent years. It provides important detection techniques for the pathogen diagnosis, monitoring and prevention of infectious diarrhea.

DETAILED DESCRIPTION

The present invention will be further described below with reference to specific examples. It should be understood that these examples are only used to illustrate rather than limit the present invention. The following examples are not used to limit the protection scope of the present invention.

Example 1 Isolation, Identification and Virulence Test of a Novel K (Capsular Antigen) Serotype of *Vibrio parahaemolyticus* (O4:KUT-recAin)

Fecal specimens from patients with acute diarrhea were introduced into alkaline peptone water, cultured for enrichment at 37° C. for 6 h, and then transferred to a TCBS medium to incubate at 37° C. for 18 h. Single colonies were selected and identified as *Vibrio parahaemolyticus* by a Bruker matrix-assisted laser desorption ionization-time of flight (MALDI TOF) mass spectrometer. The serotype of *Vibrio parahaemolyticus* was determine by the slide agglutination method using Nihon Seiken's *Vibrio parahaemolyticus* diagnostic sera (including 11 O and 69 K), with 0.85% normal saline as a negative control. *Vibrio parahaemolyticus* strains that did not agglutinate with the existing 69 types of K sera were marked as KUT.

The whole genome of the KUT strains was sequenced, and their K epitopes were analyzed to further determine that whether they are novel K serotypes of *Vibrio parahaemolyticus*. The present invention provides a novel K serotype of *Vibrio parahaemolyticus* that agglutinates with O4 sera but does not agglutinate with the existing 69 kinds of K sera, named O4:KUT-recAin strain, which was deposited at the China General Microbiological Culture Collection Center (CGMCC for short) in Beijing, China on Feb. 20, 2019 with a deposit number of CGMCC No. 17249.

Figure 1:
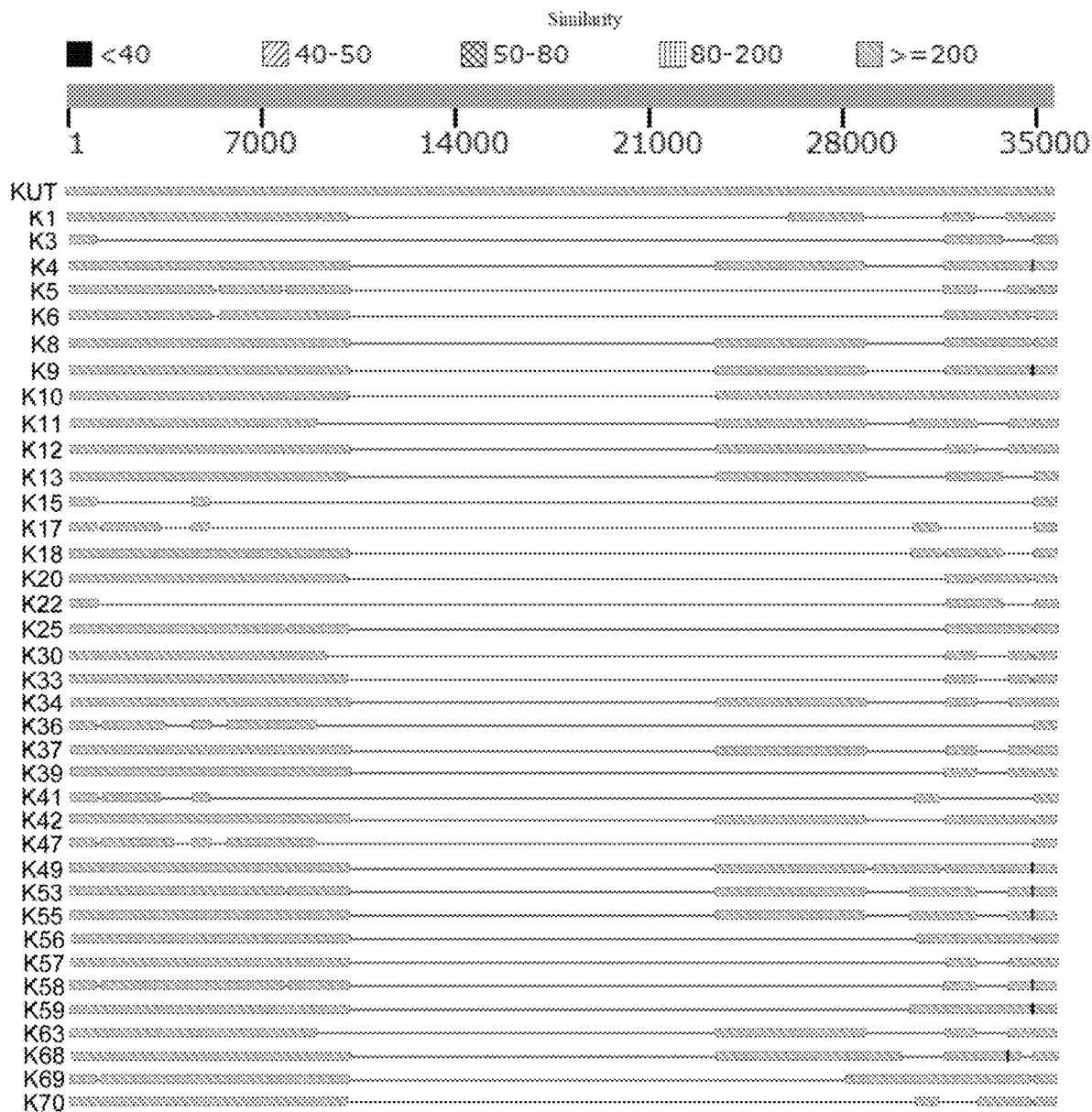
FIG. 1 is the results of similarity comparison between the K epitope sequence of *Vibrio parahaemolyticus* O4:KUT-recAin strain and 37 known K epitope sequences.

Whole genome sequencing analysis of the K epitope of the *Vibrio parahaemolyticus* O4:KUT-recAin strain found that the sequence of K epitope (see sequence 1) of this strain was different from those of current K epitopes of *V. parahaemolyticus* in the NCBI database. This further proved that this *Vibrio parahaemolyticus* is a new strain of K serotype. The similarity comparison results of the sequence of K epitope of the *Vibrio parahaemolyticus* O4:KUT-recAin strain with those of 37 known K epitopes are shown in FIG. 1.

Figure 2:
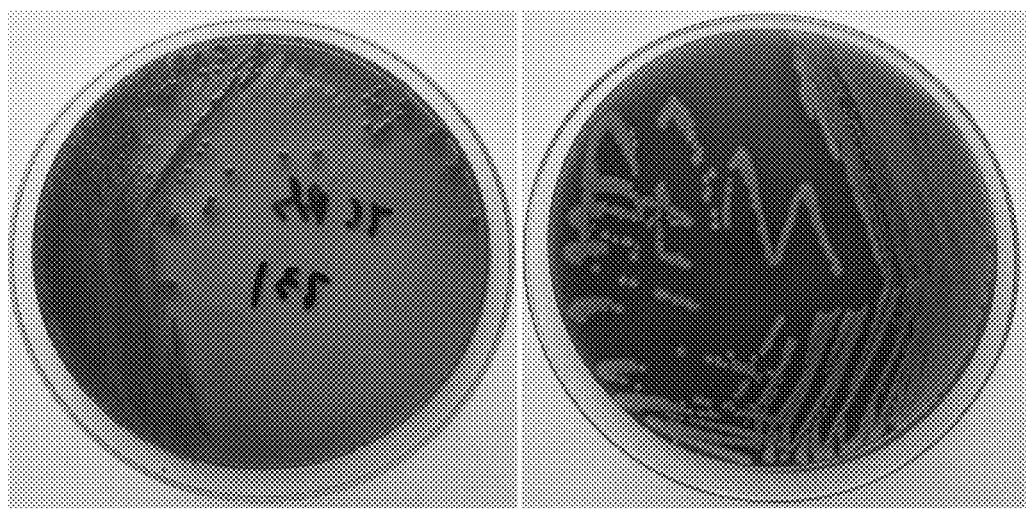
FIG. 2 shows the growth morphology of the *Vibrio parahaemolyticus* O4:KUT-recAin strain on a plate. The left picture shows the TCBS plate, and the right picture shows the Columbia blood agar plate.
Figure 3:
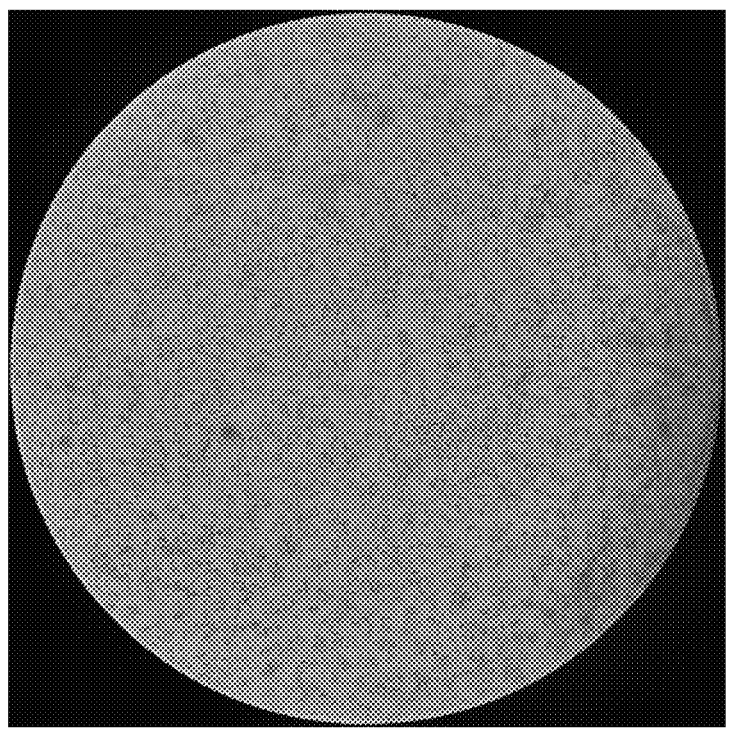
FIG. 3 is the morphology of the colonies of the *Vibrio parahaemolyticus* O4:KUT-recAin strain under a microscope after Gram staining.
Figure 4:
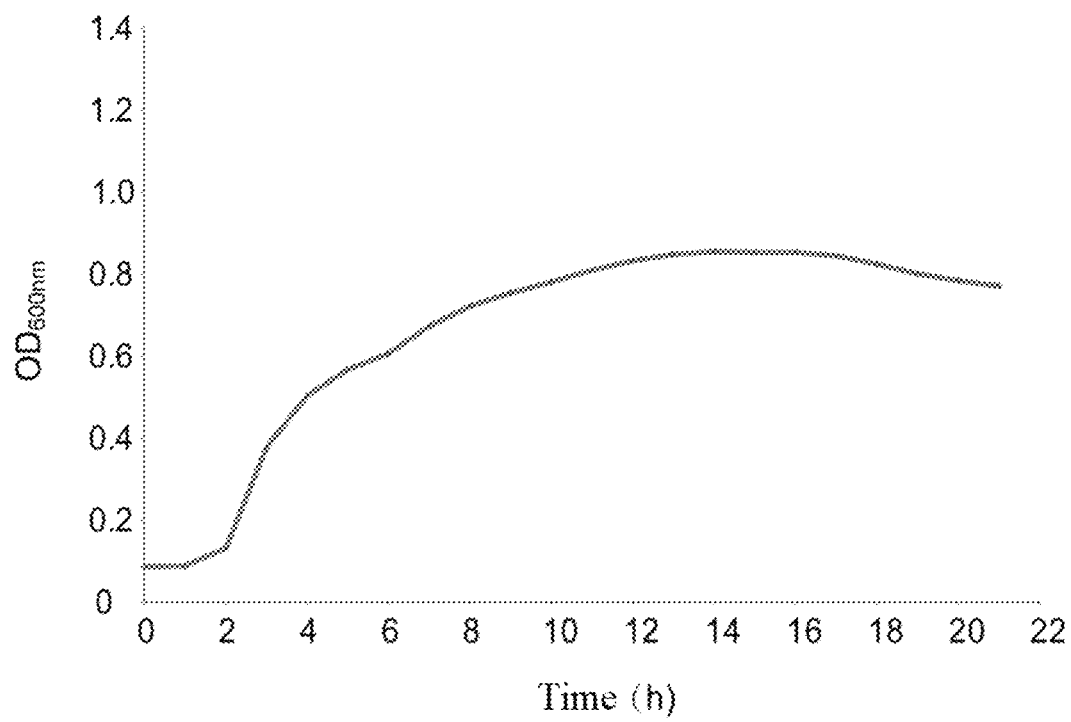
FIG. 4 is a growth curve of the *Vibrio parahaemolyticus* O4: KUT-recAin strain.

The growth morphology of the *Vibrio parahaemolyticus* O4:KUT-recAin strain on a plate is shown in FIG. 2. Well-grown colonies were picked and seeded in a BHI medium with 3% NaCl (pH=8.5) to culture at 37° C. See FIG. 4 for the growth curve. The culture characteristics of the O4:KUT-recAin strain in FIG. 4 show that the OD600 nm value of the solution started to increase about 2 h after inoculation, and reached the maximum between 14-16 h, but then began to decline with time.

Figure 5:
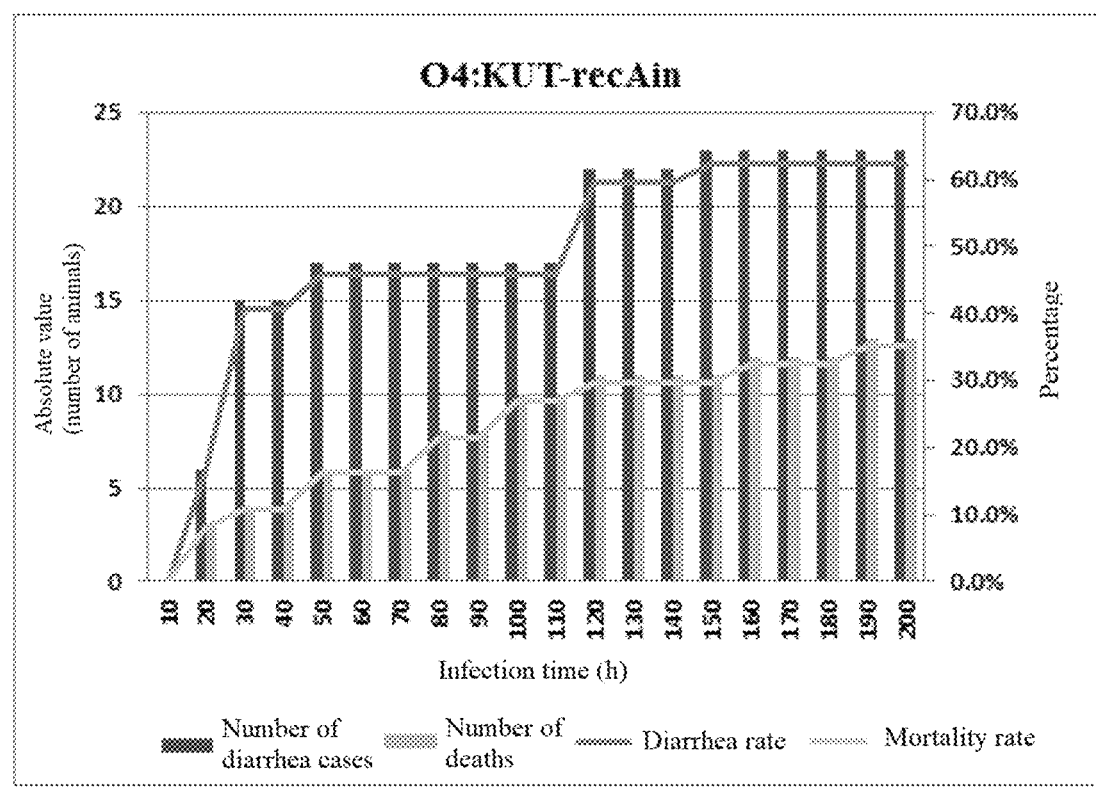
FIG. 5 shows the data of diarrhea and death in newborn rabbits fed with the *Vibrio parahaemolyticus* O4:KUT-recAin strain.

The *Vibrio parahaemolyticus* O4:KUT-recAin strain at 1×1010 CFUs was fed to 2-day-old newborn rabbits. After 20 h, the newborn rabbits developed symptoms of diarrhea, and in severe cases, suffered weight loss and even death. FIG. 5 shows the diarrhea and death data of 5 litter rabbits, 37 in total, fed with the *Vibrio parahaemolyticus* O4:KUT-recAin strain. The diarrhea rate of the newborn rabbits was 41% after 2 days, and reached 60% after 5 days. Eight days after infection, the mortality of the newborn rabbits was 35%.

Example 2 Preparation of a Novel K Serum for *Vibrio parahaemolyticus*

Preparation of antigen: the novel K serotype of *Vibrio parahaemolyticus* O4: KUT-recAin strain was seeded into a BHI medium with 3% NaCl to incubate at 37° C. overnight, centrifuged at 3000×g for 10 min to collect the bacteria. The bacteria were washed twice with normal saline, and then inactivated with normal saline containing 0.5% formaldehyde for 24 h, and centrifuged at 3000×g for 10 min to collect the inactivated bacteria. Finally, the inactivated bacteria were dissolved in normal saline for immunization of rabbits.

Immunization of rabbits: 3 healthy 12-week-old New Zealand white rabbits were acclimatized for 3 days and then immunized with the inactivated novel K serotype of *Vibrio parahaemolyticus* dissolved in 0.85% NaCl (109 CFU/ml), 4 sites (left and right sides of the back and thigh roots) for each rabbit, 250 µl for each site. The immunization was boosted once every 2 weeks in an immunization volume the same as the first immunization, 5 times in total; thereafter, the whole blood was collected from the heart.

Collection of immune serum: The collected whole blood was left at 37° C. for 2 h, transferred to 4° C. overnight, and then centrifuged at 12000×g for 10 min the next day to collect serum, which was the immune serum.

Figure 6:
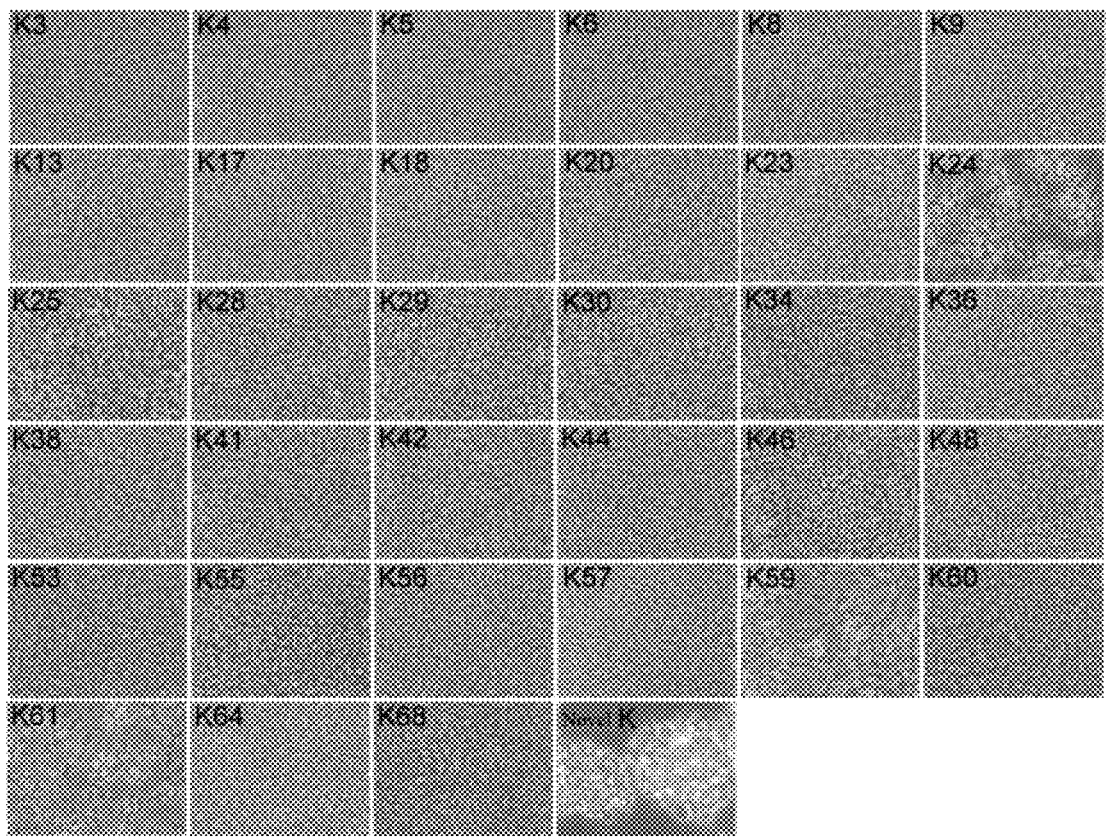
FIG. 6 shows the agglutination reaction of the immune serum for the *Vibrio parahaemolyticus* O4:KUT-recAin strain with 33 known K serotype strains.
Figure 7:
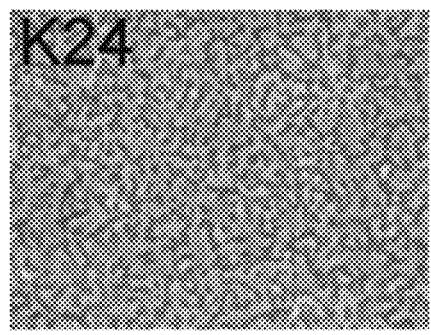
FIG. 7 shows that the immune serum for the *Vibrio parahaemolyticus* O4:KUT-recAin strain absorbed with the K24 strain inactivated by 0.5% formaldehyde does not agglutinate with the K24 strain.

Preparation of specific immune serum: The collected immune serum was subjected to a slide agglutination reaction with the novel K serotype strain. The specific steps for slide agglutination are as follows: The slide was streaked into sections using a marker and one drop (about 5 μl) of the novel K serum was added dropwise into each section, wherein in one section, normal saline was used instead of the novel K serum as a control to exclude self-agglutination. Then, 5 μl of the bacterial suspension was added to each section, and the reaction was thoroughly mixed for 1 min to observe whether there was agglutination. The agglutination of the immune serum with the novel K serotype strain was obvious. The immune serum for the novel K serotype strain cross-reacted with the K 24, K 59, and K 61 serotype strains among the known K serotype strains (FIG. 6). The immune serum was sequentially adsorbed with 109 CFU/ml K24 strain, K61 strain, and K59 strain inactivated with 0.5% formaldehyde at 4° C. for 2-24 h, and then centrifuged at 12000×g for 10 min to obtain a supernatant which was the immune serum specific to the novel K serotype strain (FIG. 7), called the novel K serum.

Example 3 Properties of the Novel K Serum

Figure 8:
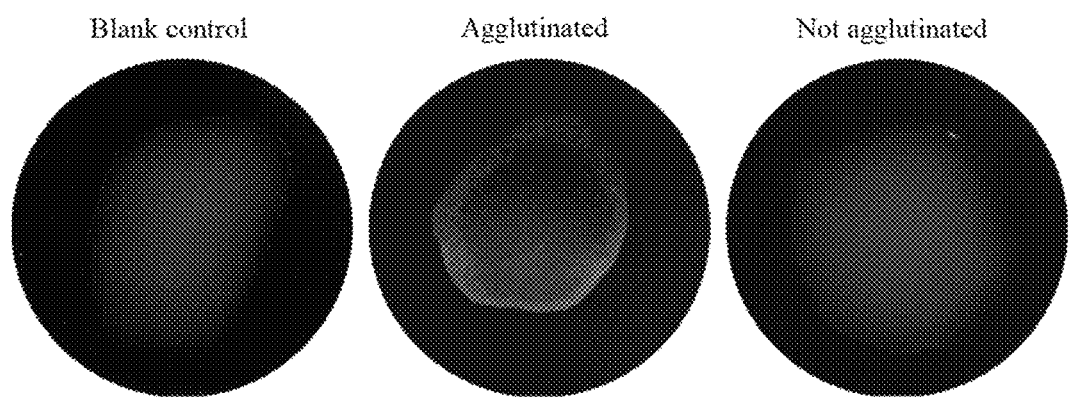
FIG. 8 shows the agglutination reaction between the novel K serum and the *Vibrio parahaemolyticus* O4:KUT-recAin strain (middle). Left: 0.85% NaCl and *Vibrio parahaemolyticus* O4:KUT-recAin strains; right: the novel K serum and the O3:K6 serotype strain.

The novel K serum and KUT strains were able to quickly detect the novel K serotype strain (O4:KUT-recAin) by agglutination (FIG. 8). The novel K serum did not agglutinate with 33 known K serotypes of *Vibrio parahaemolyticus* (Table 1), and did not agglutinate with enteric pathogens including *Vibrio cholerae, Vibrio fluvialis, Campylobacter jejuni, Campylobacter coli, Escherichia coli, Salmonella typhimurium, Salmonella typhi, Shigella dysenteriae*, and *Shigella flexneri* either (Table 2). When diluted 64-fold with normal saline by the doubling dilution method, the novel K serum still obviously agglutinated with the novel K serotype strain (O4:KUT-recAin) (Table 3). The novel K serum has good specificity and sensitivity.

TABLE 1

Agglutination of the novel K serum with different K serotypes of *Vibrio parahaemolyticus*

| No. | *Vibrio parahaemolyticus* strain | K serotype | Agglutination |
| --- | --- | --- | --- |
| 1 | VP2355 | K3 | No |
| 2 | VP378 | K4 | No |
| 3 | VP857 | K5 | No |
| 4 | VP91 | K6 | No |
| 5 | VP30 | K8 | No |
| 6 | VP473 | K9 | No |
| 7 | VP3125 | K13 | No |
| 8 | VP401 | K17 | No |
| 9 | VP797 | K18 | No |
| 10 | VP1943 | K20 | No |
| 11 | VP948 | K23 | No |
| 12 | VP2022 | K24 | No |
| 13 | VP78 | K25 | No |
| 14 | VP2481 | K28 | No |
| 15 | VP74 | K29 | No |
| 16 | VP2012 | K30 | No |
| 17 | VP1906 | K34 | No |
| 18 | VP146 | K36 | No |
| 19 | VP2626 | K38 | No |
| 20 | VP2838 | K41 | No |
| 21 | VP563 | K42 | No |
| 22 | VP649 | K44 | No |
| 23 | VP53 | K46 | No |

TABLE 1-continued

Agglutination of the novel K serum with different K serotypes of *Vibrio parahaemolyticus*

| No. | *Vibrio parahaemolyticus* strain | K serotype | Agglutination |
| --- | --- | --- | --- |
| 24 | VP2368 | K48 | No |
| 25 | VP412 | K53 | No |
| 26 | VP792 | K55 | No |
| 27 | VP192 | K56 | No |
| 28 | VP482 | K57 | No |
| 29 | VP58 | K59 | No |
| 30 | VP3116 | K60 | No |
| 31 | VP2406 | K61 | No |
| 32 | VP2399 | K64 | No |
| 33 | VP544 | K68 | No |

TABLE 2

Agglutination of the novel K serum with other intestinal pathogens

| No. | Bacteria | Agglutination |
| --- | --- | --- |
| 1 | *Vibrio cholerae* | No |
| 2 | *Vibrio fluvialis* | No |
| 3 | *Campylobacter jejuni* | No |
| 4 | *Campylobacter coli* | No |
| 5 | *Escherichia coli* | No |
| 6 | *Salmonella typhimurium* | No |
| 7 | *Salmonella typhi* | No |
| 8 | *Shigella dysenteriae* | No |
| 9 | *Shigella flexneri* | No |

TABLE 3

Agglutination of the novel K serum (doubling diluted) with the novel K serotype of *Vibrio parahaemolyticus*

| Serum | Agglutination with the novel K serotype of *Vibrio parahaemolyticus* (109 CFU/ml) |
| --- | --- |
| Pre-immune serum 1:1 | No |
| Novel K serum 1:2 | Yes |
| Novel K serum 1:4 | Yes |
| Novel K serum 1:8 | Yes |
| Novel K serum 1:16 | Yes |
| Novel K serum 1:32 | Yes |
| Novel K serum 1:64 | Yes |
| Novel K serum 1:128 | No |

Example 4 Application of the Novel K Serum

Under the support of the project of Study on the Epidemic Pattern of Infectious Diseases in Zhejiang and Surrounding Provinces (2017ZX10103008), which is one of the major national R&D projects involving prevention and treatment of major infectious diseases such as AIDS and viral hepatitis in "Thirteenth Five-Year Plan", 2368 strains of *Vibrio parahaemolyticus* from patients with acute diarrhea in Zhejiang, Jiangsu, Liaoning, Shenzhen, Shanghai and other places were collected in 2013-2017 and were subjected to slide agglutination test with the prepared novel K serum. A total of 329 novel K serotype strains (O4:KUT-recAin) were identified. Whole genome sequencing was performed on 161 of them to analyze their K epitopes. The results showed that they had the same K epitope as the *Vibrio parahaemolyticus* O4: KUT-recAin strain, that is, they are all novel K serotype of *V. parahaemolyticus* (O4:KUT-recAin). The accuracy of identifying the novel K serotype of *Vibrio parahaemolyticus*

(O4:KUT-recAin) by the slide agglutination method using the prepared novel K serum was 100%. Therefore, the novel K serum can quickly and easily identify the novel K serotype of *Vibrio parahaemolyticus* (O4: KUT-recAin).

What is claimed is:

1. A method for preparing a K serum with a *Vibrio parahaemolyticus* as an antigen, comprising:

the *Vibrio parahaemolyticus* is seeded into a BHI medium with 3% NaCl, and cultured at 37° C. overnight;

the bacteria are collected, washed twice with normal saline, and then inactivated with a normal saline solution containing 0.5% formaldehyde for 24 h, and the inactivated bacteria are then dissolved in normal saline to act as an antigen; and the K serum is prepared by injecting and immunizing an animal with the *Vibrio parahaemolyticus* as the antigen;

wherein the *Vibrio parahaemolyticus* was deposited at the China General Microbiological Culture Collection Center (Institute of Microbiology, Chinese Academy of Sciences, No. 3, Yard 1, Beichen West Road, Chaoyang District, Beijing) on Feb. 20, 2019, with a deposit number of CGMCC No. 17249, wherein the K epitope of the *Vibrio parahaemolyticus* has a sequence set forth in Sequence No. 1.

2. The method for preparing the K serum with a *Vibrio parahaemolyticus* as an antigen according to claim 1, further comprising:

healthy 12-week-old New Zealand white rabbits are selected and immunized with the inactivated *Vibrio parahaemolyticus* in 0.85% NaCl at a concentration of 109 CFU/ml, 4 sites for each rabbit and 250 μl for each site, and subsequently boosted once every 2 weeks in an immunization volume the same as the first immunization, 5 times in total;

thereafter, whole blood is collected from the heart, and the collected whole blood is left at 37° C. for 2 h, transferred to 4° C. overnight, and then centrifuged to collect serum, which is the K serum.

* * * * *